United States Patent [19]

Pfaendler et al.

[11] Patent Number: 5,108,747
[45] Date of Patent: Apr. 28, 1992

[54] STABLE OXPENEM-3-CARBOXYLIC ACIDS AS BETA-LACTAMASE INHIBITORS

[75] Inventors: Hans-Rudolf Pfaendler, Munich; Karl G. Metzger, Wuppertal; Rainer Endermann, Wuppertal; Ingo Haller, Wuppertal; Hanno Wild, Wuppertal; Wolfgang Hartiwg, Wuppertal, all of Fed. Rep. of Germany

[73] Assignee: Bayer Aktiengesellschaft, Leverkusen, Fed. Rep. of Germany

[21] Appl. No.: 413,404

[22] Filed: Sep. 27, 1989

[30] Foreign Application Priority Data

Oct. 4, 1988 [DE] Fed. Rep. of Germany ....... 3833693

[51] Int. Cl.⁵ ..................... A61K 35/66; A61K 31/42
[52] U.S. Cl. ..................................... 424/114; 514/375
[58] Field of Search .......................................... 424/114

[56] References Cited

PUBLICATIONS

Chemical Abstracts 111:39099z (1989).

*Primary Examiner*—Jerome D. Goldberg
*Attorney, Agent, or Firm*—Sprung Horn Kramer & Woods

[57] ABSTRACT

A pharmaceutical preparation comprising an antibiotic, a pharmaceutical excipient therefor, and in addition an oxapenem-3-carboxylic acid of the formula

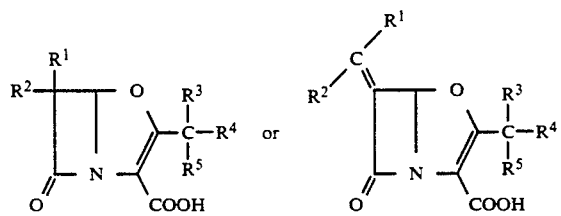

or a pharmaceutically acceptable salt, ester or amide in which $R^1$ and $R^2$ each independently is hydrogen or a pharmaceutically acceptable group having 1 to 10 carbon atoms which is connected with the balance of the molecule via carbon-carbon single bonds, and in which $R^3$, $R^4$ and $R^5$ each independently is a pharmaceutically acceptable group having 1 to 10 carbon atoms which is connected with the balance of the molecule via carbon-carbon single bonds.

9 Claims, No Drawings

STABLE OXPENEM-3-CARBOXYLIC ACIDS AS BETA-LACTAMASE INHIBITORS

The invention relates to the use of 1-oxapenem-3-carboxylic acids of the following structures

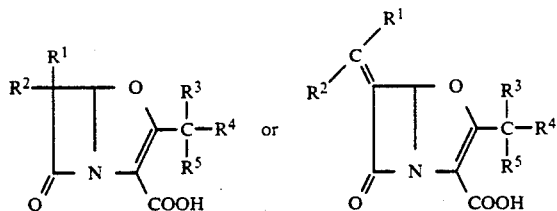

in which
$R^1$ and $R^2$ independently of one another denote hydrogen or pharmaceutically acceptable groups bonded via carbon atoms and $R^3$, $R^4$ and $R^5$ independently of one another denote pharmaceutically acceptable groups which are bonded via carbon atoms to the exocyclic, allylic carbon atom,
as β-lactamase inhibitors.

The compounds, and also their pharmaceutically acceptable salts, esters and amide derivatives, are also useful antibiotics.

The compounds according to the invention are effective β-lactamase inhibitors. β-Lactamases are enzymes which are formed by many pathogenic, clinically relevant bacteria so that they are no longer effectively inhibited by conventional antibiotics. In order to control infections with such bacteria, pharmaceutical preparations are administered in the clinics which in addition to a conventional antibiotic contain a β-lactamase inhibitor, as a rule in a 1:1 ratio. Examples are found, for example, in Chemical and Engineering News 64, (39), pages 33 to 67 (1986).

This type of β-lactamase inhibitors is not or is only slightly effective antibacterially per se; their function is the protection of a conventional antibiotic from the attacking bacterial β-lactamases.

The action as β-lactamase inhibitors of earlier prepared oxapenem-3-carboxylic acids could only be determined on cell-free enzymes because of their low hydrolytic stability. For example, the potassium salt of 2-ethyl-1-oxapenem-3-carboxylic acid was too unstable for testing synergism with ampicillin against intact bacteria (Chemistry and Biology of β-Lactam Antibiotics Vol. 2, Nontraditional β-Lactam Antibiotics, ed. by R.B. Morin and M. Gorman, Academic Press, New York, page 383 (1982)).

In contrast to these earlier prepared, unstable oxapenem-3-carboxylic acids, the stable compounds according to the invention are also fully effective as β-lactamase inhibitors in the presence of intact bacteria.

A particular advantage of the oxapenem-3-carboxylic acids according to the invention is that in addition to the abovementioned properties of β-lactamase inhibition they are also themselves antibacterially active per se. It is true that substances having similar properties are known, for example formiminothienamycin (Lit.: Recent Advances in the Chemistry of β-Lactam Antibiotics, ed. by G.I. Gregory, The Royal Society, London, page 279 (1981)). However, the compounds according to the invention show a more rapid, more progressive and more irreversible inhibition of the lactamases with many clinically relevant bacteria. Thus, for example, the cephalosporinase of E. cloacae 908 R is inhibited 780 times more effectively in vitro by the 2-tert-butyl-6-hydroxymethyloxapenem-3-carboxylic acid K salt according to the invention than by formiminothienamycin.

The oxapenem-3-carboxylic acids according to the invention can be combined with a conventional antibiotic in the ratio 1:1. The high efficacy as β-lactamase inhibitors permits, however, combinations with far lower contents of the substances according to the invention to be prepared. Thus, in most cases a ratio of 1:10 between the substances according to the invention and the conventional antibiotic is sufficient to inhibit the growth of the β-lactamase-forming bacteria rapidly and effectively in vitro. However, other ratios of 1 50 to 1:1 are also possible. The oxapenem-3-carboxylic acids according to the invention can be used in the abovementioned combinations as the racemate or in the (5R)-enantiomerically pure form.

Conventional antibiotics which can be used in pharmaceutical preparations together with the oxapenem-3-carboxylic acids according to the invention are classical (such as, for example, the penicillins and cephalosporins) and also non-classical (such as, for example, penems, catapenems or monobactams) β-lactam antibiotics. Examples of these are ampicillin, amoxicillin, azlocillin, mezlocillin, ticarcillin, cefoperazone, cephalexin, cefudor, cephaloridine, cefazolin, deftrazidine, methicillin, mecillinam, penicillin G, aztreonam, formiminothienamycin, moxalactam, etc.

Such preparations are effective against gram-positive, gram-negative, aerobic and anaerobic β-lactamase-forming and sensitive bacteria, such as, for example, staphylococci, streptococci and enterobacteria. Even actual problem bacteria, such as, for example, β-lactamase-forming Pseudomonas aeruginosa are effectively inhibited by certain preparations. It is decisive here that the conventional antibiotic with which the oxapenem-3-carboxylic acid is combined is able to penetrate into the interior of the bacterium.

Pharmaceutical preparations of penicillins and cephalosporins with the oxapenem-3-carboxylic acids according to the invention are preferred; combinations of penicillins with 2-tert-butyl-6-hydroxy-methyloxapenem-3-carboxylic acid K salt are particularly preferred.

The invention relates to 6-unsubstituted, 6-mono-or 6,6-disubstituted 1-oxapen-2-em-3-carboxylic acids which are provided with particular radicals in the 2-position. These radicals are characterized in that they have a central carbon atom which is bonded directly to the oxapenem nucleus and which holds bonded three further groups bonded via C atoms. These compounds are useful antibiotics and they can be represented by the general structural formulae

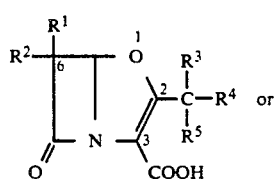

-continued

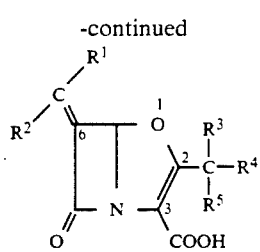

in which $R^1$ and $R^2$ independently of one another are selected from: hydrogen or the pharmaceutically acceptable groups bonded via C-C single bonds to the other part of the molecule and which contain: substituted or unsubstituted alkyl, alkenyl, alkinyl, cycloalkyl, alkylcycloalkyl, alkylcycloalkenyl, cycloalkylalkyl, alkenylcycloalkyl, cycloalkenylalkyl, aryl, aralkyl, aralkenyl, aralkinyl, carboxyl or cyano, in which the preceding alkyl, alkenyl or alkinyl parts of the molecule contain 1 to 6 carbon atoms, the cycloalkyl or the cycloalkenyl parts of the molecule contain 3 to 6 and the aryl parts of the molecule contain 6 to 10 carbon atoms. Heteroaryl, heteroaralkyl, heteroaralkenyl, heteroaralkinyl, alkylheteroaryl, heterocyclyl, heterocyclylalkyl, heterocyclylalkenyl, heterocyclylalkinyl, alkylheterocyclyl, in which the preceding alkyl, alkenyl or the alkinyl parts of the molecule contain 1 to 6 carbon atoms and the heteroaromatic or heterocyclic part of the molecule is mono- or bicyclic and contains 3 to 10 ring atoms, of which one or more are selected from the group comprising: oxygen, sulphur and nitrogen, and where the substituents of the abovementioned groups may be: protected or unprotected hydroxyl, hydroxyalkyloxy, aminoalkyloxy, amidinoalkyloxy, alkyloxy, acyloxy, aryloxy, heteroaryloxy, heterocyclyloxy, carbamoyl, carbamoyloxy, thiocarbamoyl, thiocarbamoyloxy, alkylcarbamoyloxy, alkylthiocarbamoyloxy, mercapto, alkylthio, hydroxyalkylthio, aminoalkylthio, amidinoalkylthio, acylthio, arylthio, alkylheteroarylthio, hydroxyalkylheteroarylthio, heterocyclylthio, carbamoylthio, alkylcarbamoylthio, thiocarbamoylthio, alkylthiocarbamoylthio, protected or unprotected amino or monoalkylamino, dialkylamino, oxo, protected or unprotected oximino or alkylimino, tetraalkylammonium, cycloalkylamino, arylamino, heteroarylamino, heterocyclamino, acylamino, amidino, alkylamidino, guanidino, alkylguanidino, carbamoylamino, alkylcarbamoylamino, thiocarbamoylamino, alkylthiocarbamoylamino, nitro, chlorine, bromine, fluorine, iodine, azido, cyano, alkylsulphinyl, alkylsulphonyl, sulphonamido, sulphamoyloxy, alkylsulphonyloxy or protected or unprotected sulpho, sulphoxy or carboxyl, where the substituents independently of one another occur one or more times and the alkyl part of the molecule thereof contains 1 to 6 carbon atoms, the aryl part of the molecule thereof contains 6 to 10 carbon atoms, and where the heteroaromatic or heterocyclic part of the molecule is mono- or bicyclic and contains 3 to 10 ring atoms, of which one or more are selected from the group comprising oxygen, sulphur and nitrogen, and characterized in that $R^3$, $R^4$ and $R^5$ independently of one another are selected from the previously mentioned pharmaceutically acceptable groups bonded to the other part of the molecule by carbon-carbon single bonds.

The groups $R^3$, $R^4$ and $R^5$ are independently selected from the pharmaceutically acceptable groups bonded via C-C single bonds to the other part of the molecule, as are described above.

The protective groups of the abovementioned protected substituents are easily removable radicals which are known per se, such as are customarily used for this purpose in organic synthesis. Such protective groups are found, for example, in T.W. Greene, "Protective Groups in Organic Synthesis", Wiley, New York, 1981.

Furthermore, two of the groups $R^3$, $R^4$ or $R^5$ can be together made into a bridge via carbon, oxygen, nitrogen and sulphur-containing parts of the molecule; they are then constituents of a carbocyclic or heterocyclic ring which can be three-, four-, five- or six-membered.

Furthermore, the two groups $R^1$ and $R^2$ can together be made into a bridge via carbon, oxygen, nitrogen and sulphur-containing parts of the molecule; they are then constituents of a three-, four-, five- or six-membered carbo- or heterocyclic ring.

Examples of bridging parts of the molecule for $R^1$ and $R^2$ or for $R^3$ and $R^4$ are methylene, dimethylene, trimethylene, tetramethylene, oxamethylene, oxadimethylene, dioxamethylene, azadimethylene, diazamethylene, or the like.

Pharmaceutically acceptable groups $R^1$, $R^2$, $R^3$, $R^4$ and $R^5$ which are bonded via a C-C single bond are groups which are, for example, customary in the β-lactam antibiotics. Such groups are found, for example, in M.L. Sassiver, A. Lewis in "Advances in Applied Microbiology, ed. D. Perlman, Academic Press, N.Y. (1970).

The invention furthermore relates to the pharmaceutically acceptable salts, esters and amide derivatives of the compounds (I) and (II) according to the invention.

The invention furthermore relates to processes for the preparation of these compounds (I) and (II), pharmaceutical preparations containing these compounds and methods of treatment in which these compounds and preparations are administered, if an antibiotic effect is indicated.

In addition to the classical β-lactam antibiotics, i.e. the penicillins and cephalosporins, the so-called nonclassical or non-traditional β-lactam antibiotics are also employed today against bacterial infectious diseases. The most important compounds of this type used today are the penems and the carbapenems. A book which has recently appeared deals with the synthesis and pharmacology of these new active compounds: Chemistry and Biology of β-Lactam antibiotics, Vol. 2, (Non-traditional β-Lactam Antibiotics), ed. by R.B. Morin and M. Gorman, Academic Press, New York (1982).

For reasons of the close structural relationship of the oxapenemcarboxylic acids with the sulphur-containing penemcarboxylic acids or with the carbapenemcarboxylic acids, it could be suspected that oxapenem-3-carboxylic acids would also be antibacterially effective (Tetrahedron 38 (16) 2489-2504 (1982), page 2489).

Although an antibacterial efficacy of oxapenem-3-carboxylic acids was mentioned, for example in U.S. Pat. No. 4,172,895 or EP 0,018,305 A1, it has never been supported by experimental data. The only available measurements on its antibacterial efficacy are found in "Chemistry and Biology of β-Lactam Antibiotics, Vol. 2 Nontraditional β-Lactam Antibiotics" ed. by R.B. Morin and M. Gorman, page 383;

"(The potassium salt of 2-ethyl-1-oxapenem-3-carboxylic acid) was too unstable for testing the antibacterial activity or the synergism with ampicillin against intact bacteria."

A compound put forward as effective in earlier patent applications, 2-ethyl-1-oxapen-2-em-3-carboxylic acid, was thus in reality far too unstable in aqueous medium for antibacterial testing and thereby virtually ineffective as an antibiotic. Only an inhibition of isolated bacterial enzymes ($\beta$-lactamases) was detectable.

The instability of oxapenem-3-carboxylic acids disclosed earlier, also the clavemcarboxylic acids mentioned, expressed itself also in the preparation of the methyl esters, for example in J.C.S. Chem. Commun. 1977, 720. Even these were unstable.

The low significance of the antibacterially virtually ineffective or poorly effective oxapenem-3-carboxylic acids may also be judged from the fact that in a book containing 402 pages about non-classical $\beta$-lactam antibiotics (Chemistry and Biology of $\beta$-Lactam Antibiotics, Vol. 2, ed. by R.B. Morin and M. Gorman, Academic Press, New York 1982) only 5 pages are devoted to them (pages 381–385).

Still much lower interest was shown for the oxapenem-3-carboxylic acids in the following years (1982–1986) which was confirmed by a complete literature search in Chemical Abstracts. Under the systematic name 4-oxa-1-azabicyclo[3.2.0]hept-2-ene-2-carboxylic acid, it was found that the research in this area constantly decreased: 1977: 3, 1978: 9, 1979: 2, 1980: 6, 1981: 9, 1982: 2, 1983: 5, 1984: 2, 1985: 0, 1986: 0 publications. The oxapenem-3-carboxylic acids had thus become uninteresting to the professional world because of their low stability and because of their low antibacterial efficacy. This low interest int he oxapenem-3-carboxylic acids compared with that in other non-classical $\beta$-lactam antibiotics shows that a prejudice exists in the professional world at present against the usefulness and efficacy of the oxapenem-3-carboxylic acid class of substances.

The stability of $\beta$-lactam antibiotics has always been a central problem of this class of active compound. Thus, for example, in the Second World War hundreds of thousands of soldiers died from wound infections since, because of the instability of penicillin, insufficient material could be prepared in order to cure the sick. Only later with the discovery of the more stable, crystalline penicillins (penicillin V and penicillin G) was the production from mold fungi on the thousand ton scale successful.

Even in the non-classical $\beta$-lactam antibiotics, stability plays an important role: thienamycin which at present is the most effective natural antibiotic "in vitro" is very sensitive to hydrolysis and therefore not utilizable as a therapeutic. Only recently has a suitable more stable derivatives (formiminothienamycin=MK-0787) been prepared (Lit.: Recent Advances in the Chemistry of $\beta$-Lactam Antibiotics, ed. by G.I. Gregory, The Royal Society, London, page 249 (1981)).

The conventional oxapenem-3-carboxylic acids are very unstable substances. A need therefore existed even in this class of substance to prepare stable derivatives having a greatly improved antibacterial effect which can be kept in aqueous medium long enough in order that they can reach the site of action undecomposed to kill the pathogenic bacteria.

It has now been found that oxapenem-3-carboxylic acids of the formulae I and II are much more stable than the compounds disclosed earlier. Exact measurements under physiological conditions, i.e. in aqueous phosphate buffer at pH 7.4 and 37° c. with the aid of UV spectroscopy showed a surprising dependence of the stability of the compounds III on the substitutents $R^1$, $R^2$, $R^3$, $R^4$ and $R^5$.

(III)

| Compound (III) | | Hydrolysis half life at pH 7.4, 37° C. (measure of the stability) |
|---|---|---|
| (a) | $R^a$, $R^b$, $R^c$, $R^d$, $R^e$ = CH$_3$ | 30 hours |
| (b) | $R^a$, $R^b$, $R^c$, $R^d$ = CH$_3$; $R^e$ = H | 2 hours |
| (c) | $R^a$, $R^b$, $R^c$ = CH$_3$; $R^d$, $R^e$ = H | 70 minutes |
| (d) | $R^a$, $R^b$ = CH$_3$; $R^c$, $R^d$, $R^e$ = H | 50 minutes |
| (e) | $R^a$, $R^b$, $R^c$, $R^d$, $R^e$ = H | a few minutes |

Compound IIIa is identical to I ($R^1$, $R^2$, $R^3$, $R^4$, $R^5$=CH$_3$).

By means of these measurements, it is demonstrated for the first time that groups $R^c$, $R^d$ and $R^e$ bonded via carbon cause a considerable stabilization of the oxapenem-3-carboxylic acids. Even a single group $R^c$, $R^d$ or $R^e$ =H leads to a drastic lowering of the stability.

The compound IIIe designated as preferred in earlier patent applications (for example in EP 18,305) hydrolyzes in a few minutes and could never be transported efficiently by the blood vessel (pH 7.4, 37° C.) to the site of action undamaged. However, even in vitro IIIe is virtually ineffective antibacterially because of immediate hydrolysis. Using Staphylococcus aureus DSM 1104, only an inhibition halo of a few mm was determined in the agar diffusion test after applying 250 μg of IIIe.

It has further been found that the compounds of the formulae I and II have a high activity against Staphylococcus aureus. Certain representatives are just as effective against gram-positive as against gram-negative bacteria and resistant bacteria. Thus, the compound (I) ($R^1$, $R^2$=H; $R^3$, $R^4$, $R^5$=CH$_3$), which is distinguished from the antibacterially virtually ineffective IIIe only by the additional possession of three methyl groups, gives the following inhibition halo diameters after applying 200 μg of substance in the agar diffusion test:

| | |
|---|---|
| *Staph. aureus* DSM 1104 | 45 mm |
| *Staph. aureus* 012484/77 (penicillin- and cephalosporin-resistant) | 47 mm |
| *Escherichia coli* DSM 1103 | 41 mm |

By means of suitable substitution, the activity against certain bacteria could be considerably increased. Thus, for example, the compound (I) ($R^1$=H; $R^2$=CH$_2$OH; $R^3$, $R^4$, $R^5$=CH$_3$) shows the following inhibition halo diameters after applying only 10 μg of substance:

| | |
|---|---|
| *Staph. aureus* DSM 1104 | 30 mm |
| *Staph. aureus* 012484/77 | 32 mm |
| *Escherichia coli* DSM 1103 | 30 mm |
| *Escherichia coli* W 3110 R6K (TEM 1) ($\beta$-lactamase-forming) | 29 mm |

The above data show that on the basis of the compounds according to the invention, the class of oxapenem-3-carboxylic acids previously considered as antibacterially virtually ineffective and therefore as uninteresting are for the first time in general moved up among the most effective antibacterial agents. Penicillin V (130 μg) showed only a strong inhibitory effect against Staph. aureus 1104 (42 mm) and a minimal effect against E. coli DSM 1103 (13 mm). The two other bacteria were not inhibited. Comparable data on the antibacterial activity of the natural antibiotic thienamycin are found in Journ. Amer. Chem. Soc. 100, 8004 (1978): the inhibition halo diameter after applying 25 μg of substance was 28–41 mm here using similar bacteria.

The present invention therefore has the object of making a new class of antibiotics available, which is important in human and animal therapy and in inanimate systems. These antibiotics are effective against many gram-positive, gram-negative, penicillin-resistant and cephalosporin-resistant bacteria. The prerequisite for this high activity and applicability is created by the trisubstitution of the exocyclic, allylic carbon atom or I or II with three groups $R^3$, $R^4$ and $R^5$ bonded via carbon atoms. The superior antibacterial activity of the oxapenem-3-carboxylic acids according to the invention could not be expected to this measure according to the level of knowledge. According to the invention, it is furthermore intended to provide chemical processes for the preparation of these antibiotics and their non-toxic pharmaceutically acceptable salts; pharmaceutical preparations containing these antibiotics; and treatment methods, in which these antibiotics and the preparations are administered, if an antibiotic effect is indicated.

The compounds of the above formulae I and II according to the invention are usefully prepared according to the following scheme:

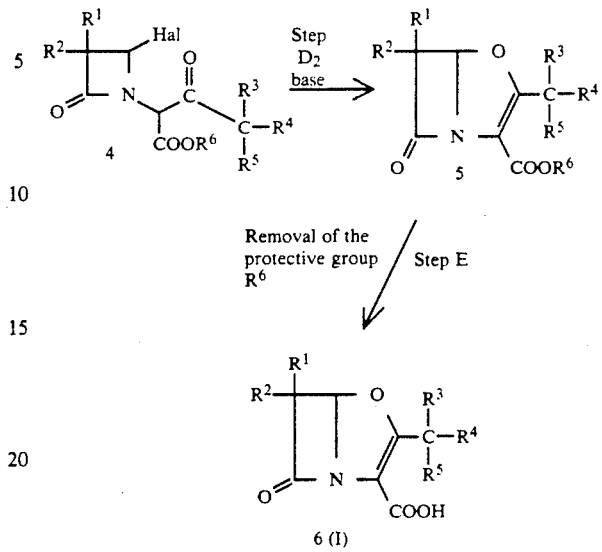

Compounds II are usefully obtained by the following reaction scheme:

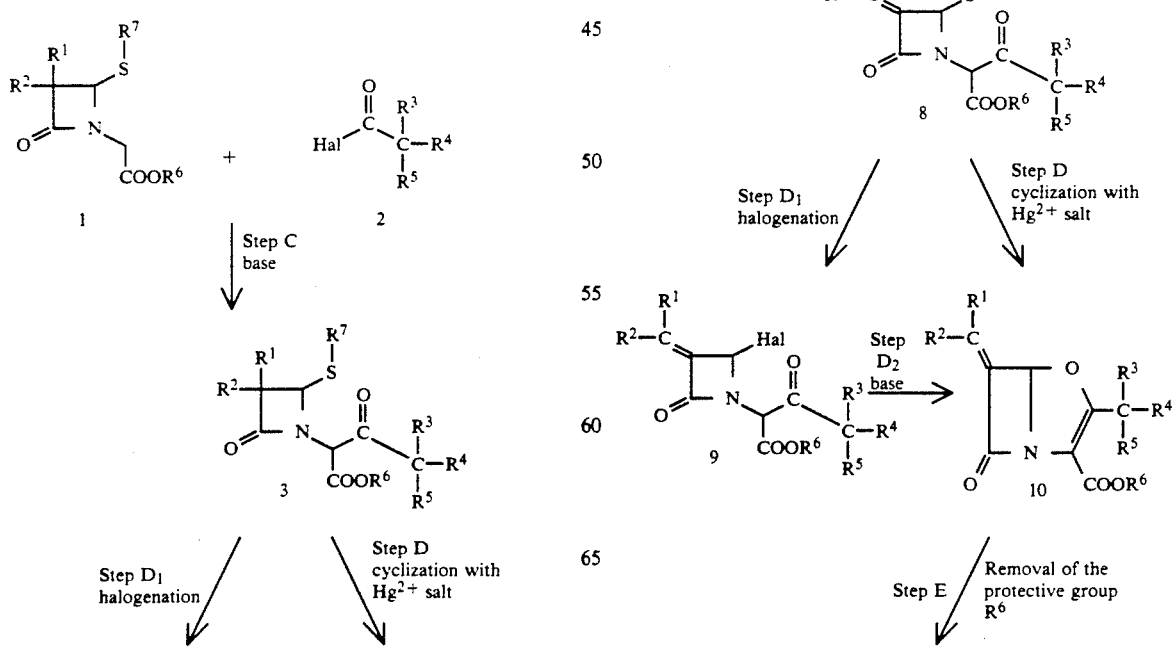

-continued

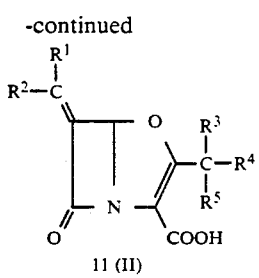

11 (II)

in which in both reaction schemes $R^1$, $R^2$, $R^3$, $R^4$ and $R^5$ have the abovementioned definitions, $R^6$ denotes an easily removable protective or masking group and where $R^6$ can also be the part of the molecule of a pharmaceutically acceptable ester. Typically, the protective group $R^6$ is an acyl group, such as lower alkanoyl, aralkylcarbonyl or the like, such as acetyl, bromo-tert-butoxycarbonyl, benzyloxycarbonyl, formyl, trifluoroacetyl and the like, or a trialkylsilyl group, such as trimethylsilyl or tertbutyldimethylsilyl; and typically the protective group $R^6$ is a substituted or unsubstituted alkyl, aralkyl, alkenyl or similar group, such as benzyl, o-nitrobenzyl, p-nitrobenzyl, trimethoxybenzyl, 2-oxopropyl, 2-oxo-2-phenylethyl, allyl, 2-cycloethyl, 2-trimethylsilyloxyethyl, 2,2,2-trichloroethyl, pivaloyloxymethyl, bromotert-butyl, and the like.

Typically, $R^7$ is a substituted or unsubstituted, branched or unbranched alkyl group, aralkyl group, aryl group, heteroaryl or heteroaralkyl group, where the substituents denote lower alkyl, acyloxy, chlorine, bromine, nitro, lower alkyloxy, cyano, and the like, and the heteroatoms of the heteroaryl or heteroaralkyl moiety are selected from the group comprising oxygen, nitrogen and sulphur. Particularly typical radicals $R^7$ are methyl, ethyl, propyl, isopropyl, butyl, phenyl, tolyl, benzyl, triphenylmethyl, tert-butyl, 2-mercaptobenzothiazolyl and the like.

The foregoing reaction diagrams are explained in greater detail as follows: A suitably substituted azetidinone (1) or (7) is reacted with the acid halide (2) using about 1 to 2 equivalents of a base such as butyllithium, lithium diisopropylamide or lithium bis(trimethylsilylamide) and the like, at a low temperature from about '170° C. to 0° C. in the course of about an hour to give 3 or 8. The identity of the solvent is not critical, provided only that the reaction participants are soluble and it is inert or substantially inert in the reaction. In the reaction (1→3) or (7→8), tetrahydrofuran, dioxane, glyme, dimethylformamide or a mixture of these solvents with hexane is usefully used.

The reaction (3→4) or (8→9) can be carried out by any known halogenation method. Suitable halogenating agents are chlorine, bromine, iodine, sulphuryl chloride and the like. In a preferred halogenating method, 3 or 8 is treated with 1 to 2 equivalents of chlorine in an inert solvent such as, for example, carbon tetrachloride, toluene or methylene chloride. Typically, this reaction is carried out at a temperature from about −70° C. to 0° C. during the course of 0.5 to 2 hours.

In the reaction (4→5) or (9→10), 4 or 9 is reacted with about 1 to 2 equivalents of a base such as, for example, sodium methoxide, potassium tert-butoxide, sodium phenoxide, sodium thiophenoxide, diazabicycloundecene and the like in a suitable inert solvent such as, for example, toluene, tetrahydrofuran or dimethylformamide to give 5 or 10. The typical reaction time is about 30 minutes to 2 hours, the typical reaction temperature about −70° C. to room temperature.

In the direct cyclization reaction (4→5) or (9→10), 4 or 9 is reacted with about 1 to 2 equivalents of a base such as, for example, sodium methoxide, potassium tert-butoxide, sodium phenoxide, sodium thiophenoxide, diazabicycloundecene and the like in a suitable inert solvent such as, for example, toluene, tetrahydrofuran or dimethylformamide to give 5 or 10. The typical reaction time is about 30 minutes to 2 hours, the typical reaction temperature about −70° C. to room temperature.

In the direct cyclization reaction (3→5) or (8→10), 3 or 8 is reacted with 1-3 equivalents of a mercury(II) salt such as, for example, mercuric chloride in a suitable inert solvent such as, for example, glyme, dioxane or tetrahydrofuran to give 5 or 10. Mixtures of two or more mercury(II) salts, for example the 1:1 mixture of mercury(II) oxide and mercury(II) chloride, are also typically used. The typical reaction temperature is 60°-100° C., the typical reaction time 2 to 20 hours.

The removal of the protective group (5→6) or (10→11) is carried out by methods which are well-known per se, such as catalytic hydrogenation, hydrolysis, reduction, nucleophilic substitution, solvolysis and the like. Suitable hydrogenation catalysts for the protective group removal include the platinum metals and their oxides, Raney nickel, palladium on charcoal and the like. Suitable solvents for the hydrogenation are methanol, ethanol, ethyl acetate/$H_2O$, ethanol/$H_2O$ and the like in the absence of hydrogen at a pressure of 1 to 50 atm. The hydrogenation typically lasts 5 minutes to 2 hours at a temperature of 0°-25° c. and is optionally carried out in the presence of a weak base, for example sodium hydrogen-carbonate. In the hydrolytic degradation of the protective group, 1 equivalent of base such as, for example, dilute aqueous sodium hydroxide solution and the like is added to 5 or 10 in a suitable solvent such as, for example, tetrahydrofuran or tetrahydrofuran/$H_2O$. Typically, the reaction lasts 5-60 minutes; the reaction temperature is −30° to 0° C. In the reductive degradation of the protective group, 1-3 equivalents of a reducing agent, for example zinc dust and the like are added to 5 or 10 in a suitable solvent, for example acetic acid/water. Typically, the reaction leasts 30 minutes to 2 hours; the reaction temperature is −30° C. to room temperature. In the degradation of the protective group by nucleophilic substitution, 5 or 10 is reacted with a nucleophilic agent, for example tetrabutylammonium fluoride, in an inert solvent, for example tetrahydrofuran. Typically, the reaction lasts 30 minutes to 2 hours; the reaction temperature is −30° C. to room temperature. In the degradation of the protective group by solvolysis, 1 to 2 equivalents of a Lewis acid, for example aluminum trichloride are added to 5 or 10 in a suitable solvent, for example tetrahydrofuran and then a solvolyzing solvent, for example water, is added. Typically, the reaction lasts 30 minutes to 2 hours; the reaction temperature is 0° C. to room temperature.

Some of the trisubstituted acetyl chlorides (2) such as, for example, pivaloyl chloride or 3-chloropivaloyl chloride are commercially available or they are known from the literature such as, for example, 2-methyl-2-phenylpropanoyl chloride (Helv. Chim. Acta 54, 870 (1971); J. Org. Chem. 39, 3268 (1974)) or 3-acetoxypivaloyl chloride (Bull, Chem. Soc. France 31, 125 (1904); J. Org. Chem. 24, 1228 (1959)) or they can be prepared in analogy to similar known substances such as, for example, 2-methyl-2-thienylpropanoyl chloride according to the synthesis directions for the phenyl derivative.

It has now surprisingly been found that the compounds of the formulae 3 or 8 and 4 or 9 exist exclusively as ketones on account of the trisubstitution of the α-carbon atom by the groups $R^3$, $R^4$ and $R^5$ bonded via carbon atoms, which was shown by the lack of NMR enol resonances at 11.6 ppm (Tetrahedron 38, (16), 2489-2504 (1982), page 2490 ) and the presence of a ketone carbonyl band at $\sim 1720$ cm$^{-1}$ and a band from a saturated carboxylic acid ester at $\sim 1755$ cm$^{-1}$ in the IR spectrum when taken up in methylene chloride. The ketone structure is also shown by a lack of reactivity: thus, these compounds, applied to a filter paper in methylene chloride and sprayed with aqueous from (III) chloride solution give no violet coloration .The ketones of the formula 3 or 8 and 4 or 9 are also not converted into the enol ether by adding diazomethane solution in ether. All these findings are in contrast to intermediate disclosed earlier without the trisubstitution according to the invention; these existed exclusively or principally as enols (for example in EP 0,018,305 A1, page 3; Tetrahedron 38, (16), 2490 (1982); J.C.S. Chem. Comm. 1977, 720, J.C.S. Chem. Comm. 1977, 905 ).

This shows that compounds of the formulae 3 or 8 and 4 or 9 have never been prepared before and never further reacted. Since the final products I or II can only be prepared via ketonic intermediates, it also shows the novelty of I and II. Admittedly, in earlier patent applications (for example in EP 0, 018, 305 Al) oxapenem-3-carboxylic acids having branched aliphatic radicals in the 2-position were mentioned. However, since these were prepared from enols, they cannot be the compounds I or II according the invention.

Using chiral azetidin-2-ones of the formula 1 or 7 having the 4R-configuration, if desired according to the described reaction schemes (1→6) or (7→11), chiral 1-oxapen-2-em-3-carboxylic acids (I) or (II) are obtained which also have the 4R-configuration.

A variant of the synthesis of compounds (I) and (II) optionally results through conversion of the groups $R^3R^4$, $R^5$ at the stage of the ketone 3 or 8. Thus, for example, a group $R^3$=alkyl-Cl can be converted into a group $R^3$ alkyl-$N_3$ using nucleophiles such as, for example, tetraalkylammonium azide. A typical solvent for the exemplary reaction is DMF. A typical reaction temperature is 0° C. to 80° C. and the reaction typically lasts for 2–48 hours.

An advantageous variant of the synthesis of compounds (I) and (II) optionally results through repeated removal of selected protective groups in the step (5→6) or (10→11). Thus, for example, protected hydroxyalkyl groups $R^1$ and $R^2$, and also protected hydroxyalkyl or protected aminoalkyl groups $R^3$, $R^4$ and $R^5$, can also be liberated identically with the removal of the protective group $R^6$.

In the following, the synthesis of the starting material 1 is described. 1 is prepared by processes known per se from 4-acyloxyazetidin-2-ones of the formula 12 or from sulphonylazetidin-2-ones of the formula 13 in the following manner:

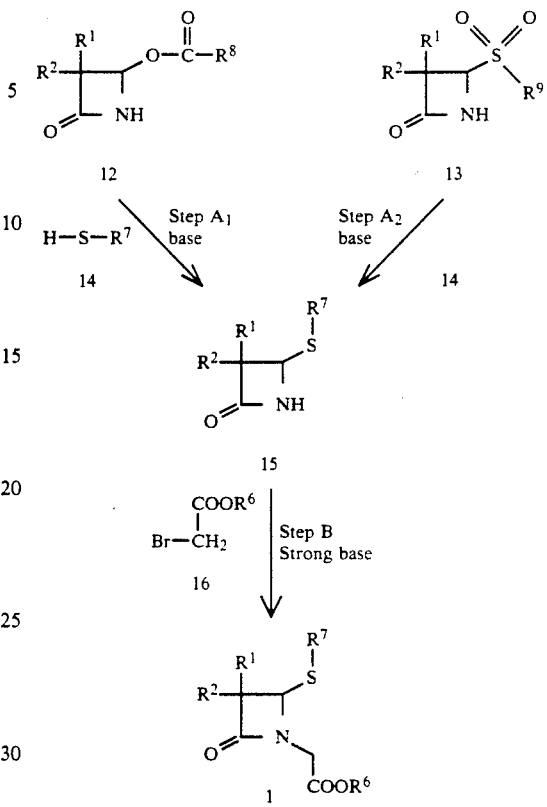

in which $R^1$, $R^2$, $R^7$ and $R^8$ have the abovementioned meanings and $R^8$ denotes an alkyl or aryl group such as, for example, methyl or phenyl, $R^9$ is typically an alkyl or aryl group, such as, for example, methyl or phenyl or a hydroxyalkyl group such as, for example, 2-hydroxyethyl, 2-hydroxyisopropyl, 2-hydroxy-1-phenylethyl or 2-hydroxytert-butyl and the like.

In the reaction (12→15) or (13→15), 12or 13 is reacted with 1–1.5 equivalents of a mercaptan (14) in a suitable solvent such as tetrahydrofuran, tetrahydrofuran/$H_2O$ or isopropanol/$H_2O$ using a base such as diazabicycloundecene or sodium hydroxide solution and the like to give 15. Typically, the reaction temperature is $-30°$ C. to room temperature and the reaction time is about 30 minutes to 4 hours.

In the reaction (15→1) 15 is reacted with a suitable bromoacetic acid ester (16) in an inert solvent such as tetrahydrofuran together with hexane using a strong base such as butyllithium, potassium tertbutoxide, lithium diisopropylamide or lithium bis-(trimethylsilylamide) and the like to give 1. Typical reaction temperatures are about $-70°$-$0°$ C., typical reaction times 30 minutes to 2 hours.

The compounds 12 can be prepared from chlorosulphonyl isocyanate and vinyl esters according to Ann. Chem. 1974, 539 but syntheses which start from penicillin are also known (for example in Recent Advances in the Chemistry of β-Lactam Antibiotics, ed. by G.I. Gregory, The Royal Society of Chemistry, London, pages 330-348 (1981)). Compounds 13 can either be prepared from 12 according to Ann. Chem. 1974, 539 or according to Journ. Amer. Chem. Soc., 102, 2039 (1980) or Recent Adv. in the Chem. of β-Lactam Antibiotics, ed. by G.I. Gregory, the Royal Society of Chemistry, London, page 368-378 (1981)), but processes for the preparation of 13 from penicillin are also known (for example Tetrahedron Lett. 22, 4141-4144 (1981)).
Using chiral azetidinones 12 or 13 having the 4R-configuration, compounds 1 having the same 4R-configuration are formed.
In the following, the synthesis of the unsaturated starting material 7 is described. 7 is expediently prepared according to the following reaction scheme:
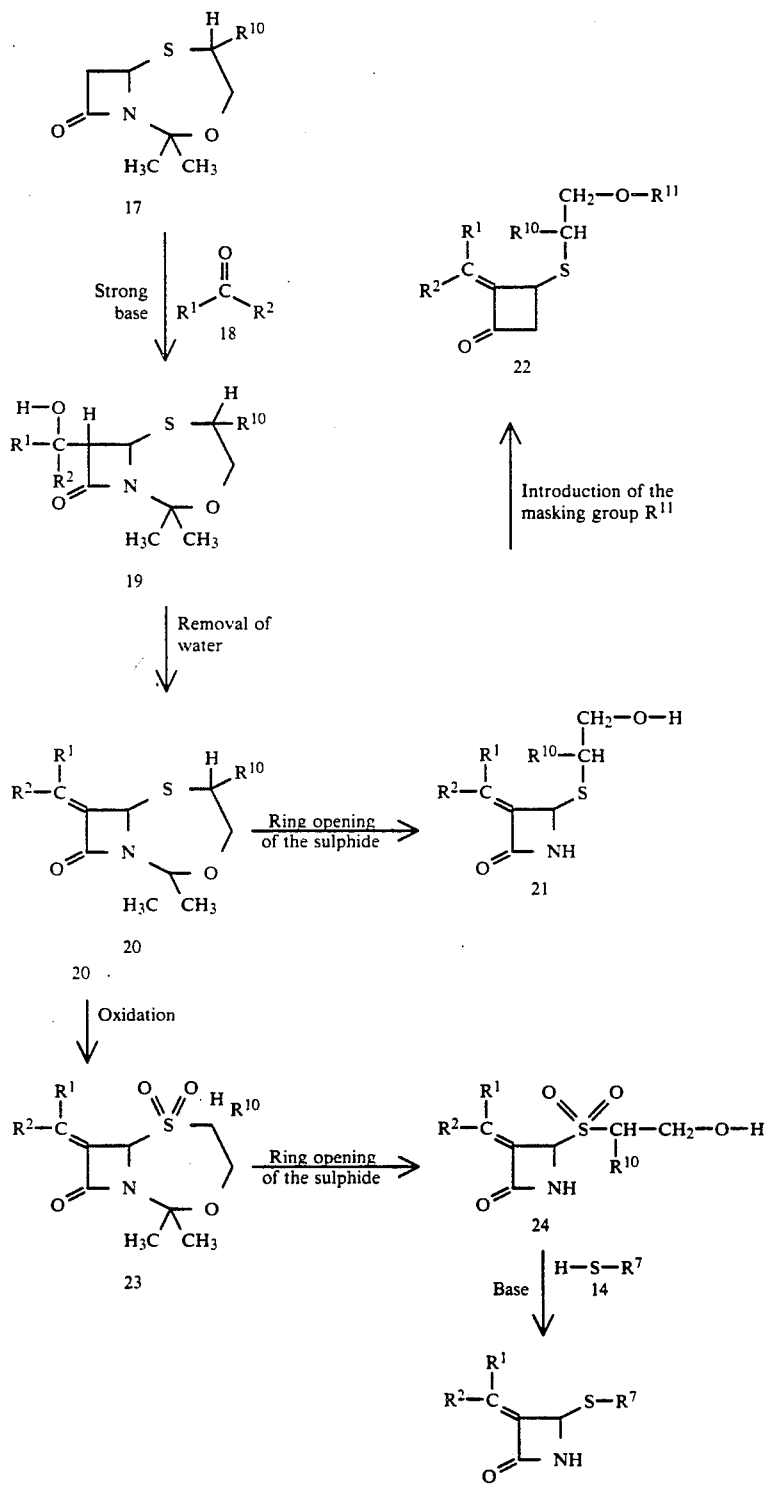

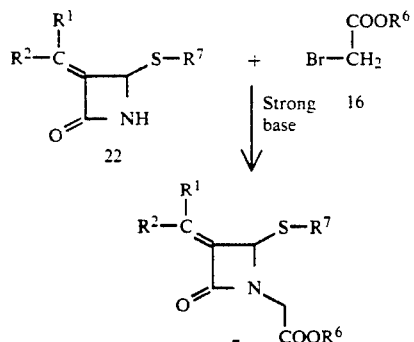

in which $R^1$, $R^2$, $R^6$ and $R^7$ have the abovementioned definitions, $R^{10}$ denotes hydrogen, an alkyl or aryl group such as, for example, methyl or ethyl and $R^{11}$ an easily introducible masking group such as alkyl, aryl, aralkyl, acyl or trialkylsilyl. Typically, $R^{11}$ is benzyl, acetyl, benzoyl, trimethylsilyl or tert-butyldimethylsilyl and the like. The identity of the masking group, however, is not particularly critical since it does not have to be removed as such but is nevertheless used again in a later reaction step, in the halogenation (8→9) or the cyclization with mercury(II) salt (8→10), as part of a removed molecule.

In the reaction (17→19), 1 to 1.2 equivalents of a strong base, such as, for example, lithium diisopropylamide and the like are added to 17 in an inert solvent, such as, for example, tetrahydrofuran ohydrofuran/-hexane and the like and then reacted with the ketone 18 to give 19. Typically, the reaction temperature is −70° C. to 0° C.; the reaction time is 30 minutes to 2 hours.

In the removal of water step (19→20) 1 to 1.5 equivalents of an acid chloride such as, for example, thionyl chloride, p-toluenesulphonyl chloride, methanesulphonyl chloride or acetyl chloride or the like and 1 to 5 equivalents of a base such as pyridine, triethylamine, N,N-dimethylaminopyridine or the like are added to 19 in an inert solvent such as, for example, tetrahydrofuran and the intermediate ester is then reacted with a strong base such as potassium tert-butoxide or diazabicycloundecene or the like in an inert solvent such as, for example, tetrahydrofuran to give 20. Typically, the reaction temperatures in both reaction steps, i.e. in the esterification and in the elimination, are −30° C. to +50° C. The reaction time of the esterification is, depending on the base strength of the base used, 2 hours to 48 hours. The reaction time of the elimination is about 30 minutes to 2 hours. More simply, the water removal step is carried out by heating 19 in an inert solvent such as toluene and the like in a water separator with the aid of a catalyst, such as, for example, p-toluenesulphonic acid or p-toluenesulphonyl chloride. At the reflux temperature of the toluene, the reaction time is typically 2–10 hours.

In the ring opening step of the sulphide (20→21) 20 is heated in an acidic solvent, such as, for example, acetic acid/$H_2O$ or the like. At the reflux temperature of about 110° C., the reaction typically lasts 30 minutes to 2 hours.

The introduction of the masking group $R^{11}$ (21→22) is carried out by conversion of 21 with 1 to 1.3 equivalents of a suitable easily introducible alkylating or acylating agent such as, for example, benzyl chloride, benzyl bromide, acetyl chloride, benzoyl chloride, trimethylchlorosilane or tert-butyldimethyl-chlorosilane in the presence of a base, such as potassium tert-butoxide, triethylamine, N,N-dimethylaminopyridine, pyridine, imidazole or the like in an inert solvent such as tetrahydrofuran or dimethylformamide and the like. Typically, the reaction temperature is about −30° C. to room temperature.

The oxidation step (20→23) is carried out by conversion of 20 using an oxidizing agent which is known per se, which can be used for sulphoxidation, such as, for example, potassium permanganate, hydrogen peroxide, m-chloroperbenzoic acid or the like. Typically, a solution of 20 in an inert solvent, such as, for example, methylene chloride, chloroform or acetone is reacted with 2 to 2.5 equivalents of an oxidizing agent such as m-chloroperbenzoic acid to give 23. Typically, the reaction temperature is −30° C. to room temperature and the reaction time is 30 minutes to 2 hours.

In the ring opening step of the sulphone (23→24) 23 is heated in an acidic solvent, such as, for example, acetic acid/$H_2O$ or the like. At the reaction temperature of about 110° C., the reaction typically lasts for 30 minutes to 2 hours.

Compounds of the formula 24 are then reacted with a mercaptan 14 in the presence of a base, such as, for example, sodium hydroxide solution and diazabicycloundecene or the like to give 22. The reaction conditions correspond to those of the reaction step (12→15).

Compounds of the formula 22 are reacted with a bromoacetic acid ester of the formula 16 with the aid of a strong base, such as, for example, butyllithium, lithium diisopropylamide or lithium bis-trimethylsilylamide to give compound 7. The reaction conditions correspond to those of the reaction step (15→1).

The compounds 17 are producible according to Recent Adv. in the Chem. of β-Lactam Antibiotics, ed. by G.I. Gregory, the Royal Society of Chemistry, London, page 368–378 (1981) or according to Tet. Lett. 22, 4141–4144 (1981). Using chiral starting material 17 having the 7R-configuration results in the conversion (17→7) to chiral 7 having the same 4R-configuration.

In the general description of the present invention, the groups $R^1$ and $R^2$ are preferably selected from hydrogen, alkyl, protected or unprotected hydroxyalkyl or protected or unprotected dihydroxyalkyl having up to 6 carbon atoms. $R^3$, $R^4$ and $R^5$ are preferably selected from substituted or unsubstituted alkyl, alkenyl, alkinyl, cycloalkyl, alkylcycloalkyl, cycloalkylalkyl, alkenylcycloalkyl, cycloalkenylalkyl, aryl, aralkyl, aralkenyl and aralkinyl, in which the preceding alkyl, alkenyl or alkinyl parts of the molecule contain 1 to 6 carbon atoms, the cycloalkyl or the cycloalkenyl parts of the molecule contain 3 to 6 and the aryl parts of the molecule contain 6 to 10 carbon atoms; heteroaryl, heteroaralkyl, heteroaralkenyl, heteroaralkinyl, alkylheteroaryl, heterocyclyl, heterocyclylalkyl, heterocyclylalkenyl, heterocyclylalkinyl and alkylheterocyclyl, in which the preceding alkyl, alkenyl or the alkinyl parts of the molecule contain 1 to 6 carbon atoms and the heteroaromatic or heterocyclic part of the molecule is mono- or bicyclic and contains 3 to 10 ring atoms, of which one or more are selected from the group comprising oxygen, sulphur and nitrogen, and where the substituents of the abovementioned groups may be protected or unprotected hydroxyl, hydroxyalkoxy, aminoalkyloxy, amidinoalkyloxy, alkyloxy, acyloxy, aryloxy, heteroaryloxy, heterocyclyloxy, carbamoyl, carbamoyloxy, thiocarbamoyl, thiocarbamoyloxy, alkylcarbamoyloxy, alkylthiocarbamoyloxy, mercapto, alkylthio, hydroxyalkylthio, aminoalkylthio, amidinoalkylthio, acylthio, arylthio, alkylheteroarylthio, hydroxyalkylheteroarylthio, heterocyclylthio, alkylthiocarbamoylthio, protected or unprotected amino or monoalkylamino, dialkylamino, oxo, protected or unprotected oximino or alkylimino, tetraalkylammonium, cycloalkylamino, arylamino, heteroarylamino, heterocyclyamino, acylamino, amidino, alkylamidino, guanidino, alkylguanidino, carbamoylamino, alkylcarbamoylamino, thiocarbamoylamino, alkylthiocarbamoylamino, nitro, chlorine, bromine, fluorine, iodine, azido, cyano, alkylsulphinyl, alkylsulphonyl, sulphonamido, sulphamoyloxy, alkylsulphonyloxy or protected or unprotected sulpho, sulphoxy or carboxyl, where the substituents occur one or more times and the alkyl part of the molecule thereof contains 1 to 6 carbon atoms, the aryl part of the molecule thereof contains 6 to 10 carbon atoms, and where the heteroaromatic or heterocyclic part of the molecule is mono- or bicyclic and contains 3 to 10 ring atoms, of which one or more are selected from the group comprising oxygen, sulphur and nitrogen.

A particularly preferred class of compound is that in which $R^1$ and $R^2$ independently of one another denote hydrogen, alkyl, protected or unprotected hydroxyalkyl or protected or unprotected dihydroxyalkyl having up to 6 carbon atoms, $R^3$ and $R^4$ denote methyl and $R^5$ is selected from amongst the groups comprising:

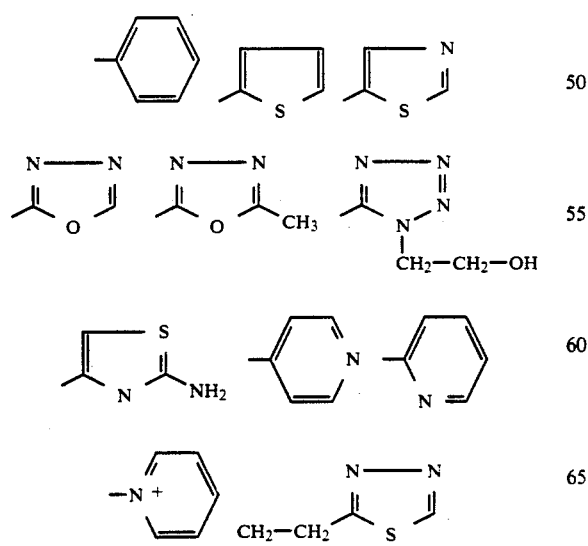

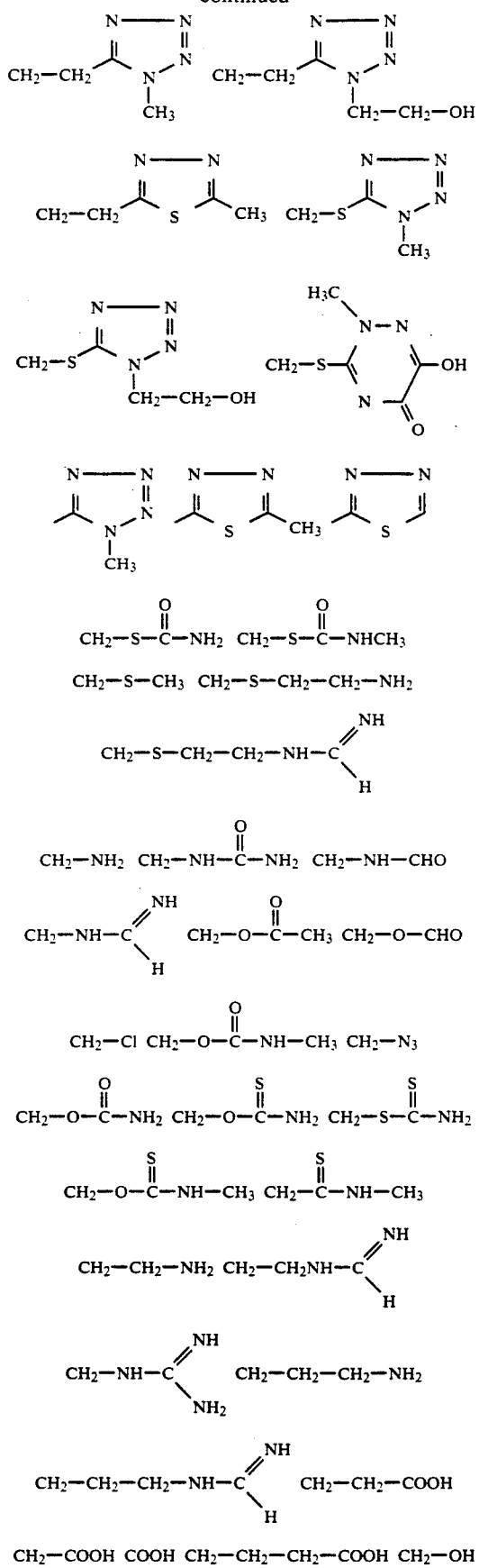

-continued

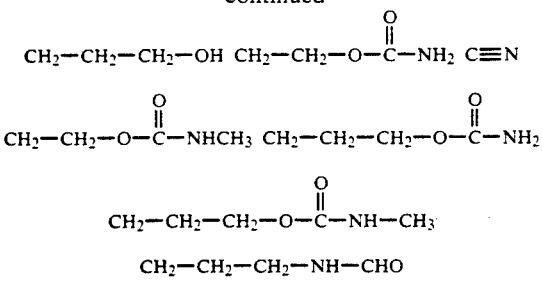

$CH_2-CH_2-CH_2-NH-CHO$

Preferred esters which are used as protective groups are those in which $R^6$ denotes benzyl, p-nitrobenzyl, methyl, tert-butyl, diphenylmethyl, trimethylsilyl, tert-butyldimethylsilyl or trichloroethyl, or $R^6$ denotes the pharmaceutically acceptable ester parts of the molecule, such as pivaloyloxymethyl, allyl, methallyl, 2-hydroxyethyl, 2-hydroxypropyl, (2-methylthio)-ethyl or 3-buten-1-yl.

Preferred protective groups for the protected hydroxyalkyl and dihydroxyalkyl groups $R^1$ and $R^2$ are benzyl, p-nitrobenzyl, benzyloxycarbonyl, p-nitrobenzyloxycarbonyl, trimethylsilyl, tert-butyldimethylsilyl, benzylidene and oxomethylene.

Preferred protective groups for the protected substituents of $R^3$, $R^4$ and $R^5$ are identical with those previously mentioned.

The products (I) and (II) according to the invention form a large number of pharmacologically acceptable salts with inorganic and organic bases. These include, for example, metal salts which are derived from alkali metal or alkaline earth metal hydroxides, carbonates or bicarbonates, and salts which are derived from primary, secondary or tertiary amines, such as monoalkylamines, dialkylamines, trialkylamines, lower alkanolamines, di-lower alkanolamines, lower alkylenediamines, N,N-diaralkyl lower alkylenediamines, aralkylamines, amino-substituted lower alkanols, N,N-di-lower alkylamino-substituted lower alkanols, amino-, polyamino- and guanidino-substituted lower alkanoic acids and nitrogen-containing heterocyclic amines. Examples of salts are those which are derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethyl-aminoethanol, 2-amino-2-methyl-1-propanol, theophylline, N-methylglucamine and the like.

The invention furthermore relates to salts of amino groups which are contained on the side chains of $R^3$, $R^4$ and $R^5$ in certain species I and II. Such pharmaceutically acceptable acid addition salts are derived from organic and inorganic acids, such as HCl, HBr, citric acid, tartaric acid and the like.

The salts can be monosalts, such as the monosodium salt, which is obtained by treatment of 1 equivalent of sodium hydroxide with 1 equivalent of the products (I) and (II), and also mixed disalts. Such salts can be obtained by treatment of 1 equivalent of a base having a divalent cation, such as calcium hydroxide, with 1 equivalent of the products (I) and (II). The salts according to the invention are pharmacologically acceptable, non-toxic derivatives which can be used as active constituents in suitable pharmaceutical dose unit forms. They can also be combined with other medicaments with the formation of preparations having a wide spectrum of activity.

The new stable oxapen-2-em-carboxylic acids according to the invention are useful antimicrobial substances which are effective against various gram-positive and gram-negative pathogens. The free acid and in particular its salts, such as the amine and metal salts, in particular the alkali metal and alkaline earth metal salts, are useful bactericides and can be employed for the removal of sensitive pathogens from dental and medicinal instruments, for the separation of microorganisms and for therapeutic use in humans and animals. For this latter purpose, pharmacologically acceptable salts with inorganic and organic bases, such as are known per se and used in the administration of penicillins and cephalosporins, are used. For example, salts, such as alkali metal and alkaline earth metal salts, and primary, secondary and tertiary amine salts may be used for this purpose. These salts may be used for pharmaceutically acceptable liquid and solid excipients with the formation of dose unit forms such as pills, tablets, capsules, suppositories, syrups, elixirs and the like, which may be prepared by processes which are known per se.

The new compounds are useful antibiotics against various gram-positive and gram-negative bacteria and are accordingly used in human and veterinary medicine. The compounds according to the invention may be used as antibacterial medicaments for the treatment of infections which are caused by gram-positive or gram-negative bacteria, for example against Staphylococcus aureus, Escherichia coli, Klebsiella pneumoniae, Bacillus subtilis, Salmonella typhosa, Pseudomonas and Bacterium proteus.

The antibacterial agents according to the invention may furthermore be used as additives for animal feeds, for the preservation of foodstuffs or feeds and as disinfectants. For example, they can be used in aqueous preparations in concentrations in the range from 0.1 to 100 parts of antibiotic/million parts of solution for the destruction and inhibition of the growth of harmful bacteria on medicinal and dental instruments and as bactericides in industrial applications, for example in water-based paints and in soft water for paper mills, and for the inhibition of the growth of harmful bacteria.

The products according to the invention can be used alone or together as active constituents in any large number of pharmaceutical preparations. These antibiotics and their corresponding salts may be used in capsule form or as tablets, powder or liquid solutions or as suspensions or elixirs. They may be administered orally, intravenously or intramuscularly.

The preparations are preferably administered in a form suitable for absorption through the gastrointestinal tract. Tablets and capsules for oral administration may be present in dose unit form and may contain customary pharmaceutical excipients, such as binders, for example syrup, acacia gum, gelatin, sorbitol, tragacanth or polyvinylpyrrolidone; fillers, for example lactose, sugar, maize starch, calcium phosphate, sorbitol or glycerol; lubricants, for example magnesium stearate, talc, polyethylene glycol, silica; disintegrants, for example potato starch, or acceptable wetting agents, such as sodium lauryl sulphate. The tablets may be coated by processes which are well known per se. Oral and liquid preparations may be present in the form of aqueous or oily suspensions, solutions, emulsions, syrups, elixirs etc., or they may be present as a dry product, for example for reconstitution with water or other suitable excipients before use. Such liquid preparations may contain additives which are known per se, such as suspending agents, for example sorbitol syrup, methylcellulose, glucose/sugar syrup, gelatin, hydroxyethylcellulose, carboxymethylcellulose, aluminium stearate gel, or hydrogenated edible oils, for example almond oil, fractionated coconut oil, oily esters, propylene glycol or ethyl alcohol; preservatives, for example methyl or propyl p-hydroxybenzoate or sorbic acid. Suppositories may contain suppository foundations which are known per se, for example cocoa butter or other glycerides.

Preparations for injection may be present in dose unit form in ampoules or in containers having a number of doses together with an added preservative. The preparations may be present in the form of suspensions, solutions or emulsions in oily or aqueous excipients, and they may contain formulating agents, such as suspending agents, stabilizers and/or dispersants. Alternatively, the active constituent may be present in powder form for reconstitution with a suitable excipient, for example sterile, pyrogen-free water, before use.

The preparations may also be present in a suitable form for absorption by the mucous membranes of the nose and the throat or the bronchial tissue, and they may usefully be present in the form of powders or liquid sprays or inhalants, pastilles, as painting agents for the throat, etc. For medication of the eyes and ears, the preparations may be used in liquid or semi-solid form in the form of individual capsules, or they may be used as drops or the like. Topical applications may be present or formulated in hydrophobic or hydrophilic foundations such as ointments, creams, lotions, painting agents, powders and the like.

The preparations according to the invention may additionally contain another constituent, such as stabilizers, binders, antioxidants, preservatives, lubricants, suspending agents, viscosity enhancers or flavor enhancers and the like additionally to the excipient. Other active constituents may additionally be contained in the preparations so that a wider spectrum of antibiotic activity is obtained.

For veterinary medicine, the preparations may, for example, be formulated as an intramammary preparation in either long-acting or rapid-release foundations.

The dose to be administered depends to a large extent on the condition of the subject to be treated and the weight of the host, and the route and frequency of administration. The parenteral route is preferred for generalized infections and the oral route for intestinal infections. In general, a daily oral dose contains about 15 to about 200 mg of active constituent/kg of body weight of the subject in one or more administrations per day. A preferred daily dose for adult humans is in the range of about 40 to 120 mg of active constituent/kg of body weight.

The preparations according to the invention may be administered in various unit dose forms, for example in solid or liquid, orally absorbable dose forms. The preparations per unit dose may contain 0.1 to 99 % of active material either in solid or liquid form. The preferred range is about 10 to 60 %. The preparations may in general contain 15 to about 1500 mg of active constituent, however in general it is preferred to use a dose in the range from about 250 to 1000 mg. With parenteral administration, the unit dose is normally the pure compound in a sterile water solution or may be present in the form of a soluble powder which can be dissolved.

Determination of β-lactamase activity

Methods: the degradation of mezlocillin was determined with Streptococcus pyogenes W using the agar hole test, the sensitivity limits of which are below 1 mcg/ml.

The colony-forming capacity of the bacteria was determined by plating out the bacteria on OXOID Iso Sensitest Agar. The two methods are international standard methods.

Degradation of mezlocillin by beta lactamase and prevention of this degradation by oxapenem "O"

|  | Mezlocillin in mcg/ml Reaction time (min) | | | |
|---|---|---|---|---|
|  | 0 | 30 | 60 | 240 |
| Beta lactamase from Pseudomonas aeruginosa W: without oxapenem | 100 | 35 | 0 | |
| with 1 mcg of oxapenem | 100 | 100 | 100 | |
| with 1 mcg of clavulanic acid | 100 | 40 | 0 | |
| with 10 mcg of clavulanic acid | 100 | 27 | 0 | |
| Beta lactamase from E. coli 4787 TEM 1: without oxapenem | 100 | 65 | 43 | 0 |
| with 10 mcg of oxapenem | 100 | 100 | 100 | |

Synergistic effect of the combination. Decrease in the colony-forming capacity of Staphylococcus aureus 25, 455/1 by the action of mezlocillin in liquid nutrient medium.

|  | Number of colonies after an action time of 6 hrs (N/ml) |
|---|---|
| Control | $3.5 \times 10^8$ |
| 0.1 mcg of oxapenem | $1.4 \times 10^8$ |
| 2.0 mcg of mezlocillin | $1.0 \times 10^6$ |
| 0.1 mcg of clavulanic acid | $1.0 \times 10^8$ |
| 2.0 mcg of mezlocillin plus 0.1 mcg of clavulanic acid | $5.5 \times 10^4$ |
| 2.0 mcg of mezlocillin plus 0.1 mcg of oxapenem | $4.0 \times 10^2$ |

The following examples illustrate the products, processes, preparations and treatment methods according to the invention.

EXAMPLE 1

Preparation of 2-tert-butyl-1-oxapen-2-em-3-carboxylic acid, its p-nitrobenzyl ester and its sodium salt

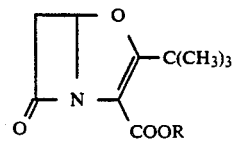

R = H, CH$_2$C$_6$H$_4$NO$_2$, Na

Step A$_1$: tert-Butylthioazetidin-2-one

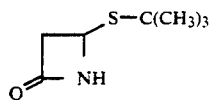

13.13 g of diazabicycloundecene (DBU) are added dropwise with stirring at −3° C. in the course of 35 minutes to a solution of 9.689 g (75 mmol) of 4-acetoxyazetidin-2-one and 7.76 g (86 mmol) of tert-butylmercaptan in 75 ml of dry THF so that the reaction temperature does not rise above −1.5° C. After keeping overnight at 0° C., the mixture is stirred for a further 1.5 hours at room temperature. Dilution with 500 ml of methylene chloride, washing with 100 ml of saturated aqueous sodium chloride solution, with 100 ml of 2 N hydrochloric acid and a further 100 ml of sodium chloride solution, drying the organic phase over magnesium sulphate and evaporating the solvent in vacuo gives a solid residue which is chromatographed on 300 g of silica gel using toluene/ethyl acetate 2:1. After recrystallizing the chromatographed product from methylene chloride/hexane, 6.5 g of pure title compound of melting point 119°-121° C. are obtained. IR spectrum in methylene chloride: 3410, 2955, 2905, 2865, 1770, 1460, 1410, 1370, 1160, 970, 925 cm$^{-1}$.

Alternative preparation of tert-butylthioazetidin-2-one from 4-benzoyloxyazetidin-2-one 41.25 ml (82.5 mmol) of 2 N NaOH in water are added dropwise at 0° C. to a solution of 9.3 ml (82.5 mmol) of tert-butylmercaptan in 37.5 ml of acetonitrile. In the course of 25 minutes, a solution (warming) of 14.32 g (75 mmol) of 4-benzoyloxyazetidin-2-one in 56 ml of acetonitrile is then added dropwise so that the reaction temperature does not rise above 0° C. The intermediate precipitate formed in the dropwise addition dissolves completely on further stirring at 0° C. The mixture is then allowed to stand overnight at 0° c., whereupon thin layer chromatography on silica gel using toluene/ethyl acetate (1:1) no longer indicates starting material. 500 ml of methylene chloride are added to the yellow reaction solution, and the aqueous phase is separated off and extracted again using 100 ml of methylene chloride. The combined extraction solutions are washed successively with 100 ml each of 1 N HCl solution, twice with NaHCO$_3$ solution and once with dilute NaCl solution. Drying the organic phase over MgSO$_4$, filtering and evaporating the solvent in vacuo yields 11.8 g (99%) of a yellow crystalline residue. Recrystallization from 160 ml of dibutyl ether at 90° C.→0° C. yields 10.3 g (86%) of pure title compound of melting point 119°-120° C.

Step B: p-Nitrobenzyl (4-tert-butylthio-2-oxo-1-azetidinyl)-acetate 14.4 ml of 1 N solution of lithium bis-trimethylsilylamide in tetrahydrofuran (THF) are added dropwise with stirring at −70° C. to a solution of 1.91 g (12 mmol) of tert-butylthioazetidin-2-one in 6 ml of dry N,N-dimethylformamide (DMF) and then a solution of 4.93 g (18 mmol) of p-nitrobenzyl bromoacetate in 6 ml of DMF is added dropwise to the mixture and the mixture is stirred at −30° C. for a further 30 minutes. Dilution of the reaction mixture with 100 ml of toluene, washing with three portions of 50 ml each of water, drying the organic phase over magnesium sulphate and evaporating the solvent in vacuo yields 4.3 g of solid crude product, which is chromatographed on 120 g of silica gel using toluene/ethyl acetate (4:1). The purified product (2.6 g) is recrystallized from 100 ml of dry isopropanol.

Yield: 2.09 g of melting point 82.5°-84° C. IR spectrum in methylene chloride: 2955, 1770, 1755, 1610, 1530, 1390, 1375, 1365, 1345, 1180, 1110, 945, 915, 855, 845 cm$^{-1}$.

Step C: p-Nitrobenzyl 2-(4-tert-butylthio-2-oxo-1-azetidinyl)-4,4-dimethyl-3-oxopentanoate

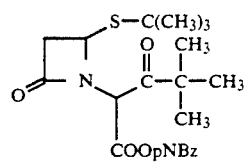

6 ml of a freshly prepared 1 M solution of lithium bis-trimethylsilylamide in THF are added dropwise at −70° C. to a solution of 1.059 mg (3 mmol) of p-nitrobenzyl (4-tert-butylthio-2-oxo-1-azetidinyl)-acetate in 7 ml of dry THF and then a solution of 382 mg of pivaloyl chloride in 1 ml of THF is added dropwise at −70° C. and the reaction mixture is further stirred at the same temperature during the course of 30 minutes. The mixture is diluted with 200 ml of toluene and a little aqueous acetic acid is added. Washing the organic phase with 100 ml of 2 N aqueous hydrochloric acid and washing twice with saturated sodium chloride solution (100 ml), drying the organic phase with MgSO$_4$ and evaporating the solvent in vacuo yields a dark red oil. Purification of the crude product on 40 g of silica gel using toluene/ethyl acetate (9:1) yields 795 mg of a non-crystalline solid. IR spectrum in methylene chloride: 2970, 1770, 1760, 1715, 1610, 1530, 1350, 1315, 1180, 995, 845 cm$^{-1}$.

Step D : p-Nitrobenzyl 2-(4-chloro-2-oxo-1-azetidinyl)-4,4-dimethyl-3-oxopentanoate

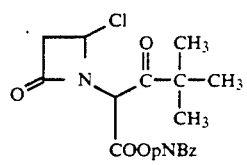

A solution of 439 mg (1.0 mmol) of p-nitrobenzyl 2-(4-tert-butylthio-2-oxo-1-azetidinyl)-4,4-dimethyl-3-oxopentanoate in 20 ml of dry methylene chloride is cooled to −50° C. and a solution of 166 mg of chlorine in 1.6 ml of carbon tetrachloride is added. After stirring for 30 minutes at −50° C., the solvent is evaporated in vacuo and the residue is recrystallized from methylene chloride/hexane, the product (348 mg) being obtained as a crystalline solid as a 6:4 mixture of the two diastereomeric title compounds.

Melting point 96°-100.5° C., decomposition $^1$H-NMR (CD$_3$CN); δ=1.04 (s, ~5.4 H, t-butyl I), 1.21(s, ~3.6 H), t-butyl II), 3.05-3.86 (m, 1H, 3'-H), 5.29 (s, 2 H, —O—CH$_2$—Ar), 5.52 (s,~0.6 H, 2-H, I), 5.71 (s,~0.4, 2-H, II), 5.84 (dd J=2 Hz, J=2 Hz, J=4 Hz ~0.6 H,4'-H, I , 5.98 (dd, J=2 Hz, J=4 Hz,~0.4 H, 4'-H, II), 7.51 (d, J=b 9 Hz,~0.8 H, Ar-H, II), 7.55 (d, J=9 Hz,~1.2 H, Ar-H, I), 8.19 (d, J=9 Hz, 2 H, Ar-H, I and II).

Step D₂: p-Nitrobenzyl 3-tert-butyl-7-oxo-4-oxa-1-aza-bucyclo[3.2.0]-hept-2-ene-2-carboxylate

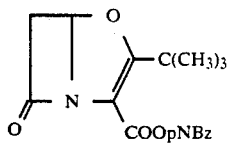

The mixture of the diastereomeric p-nitrobenzyl 2-(chloro-2-oxo-1-azetidinyl)-4,4-dimethyl-3-oxopentanoates (348 mg, 0.91 mmol) was dissolved in dry THF (10 ml) and 0.91 ml of a freshly prepared 1 M solution of potassium tert-butoxide in tert-butanol was added at 0° C. and the reaction mixture was stirred at 0° C. during the course of 15 minutes. Dilution with 150 ml of benzene, washing three times with 50 ml each of 0.5 M phosphate buffer solution pH =7, drying the organic phase over MgSO₄ and evaporating the solvent in vacuo yields a pale yellow solid which is chromatographed on 9 g of silica gel using benzene/ethyl acetate 97:3, 237 mg of product being obtained. Recrystallization from methylene chloride hexane yields 200 mg of pale yellow crystals of melting point 142°-144° C.

¹H-NMR (CD₃CN): δ=1.29 (s, 9 H, tert-butyl), 3.40 (dd, J=17 Hz, J=1 Hz, 1 H, 6-H trans-position), 3.79 (dd, J=17 Hz, J=2.5 Hz, 1 H, 6-H cis-position), 5.16 (d, J=14 Hz, 1 H, —O—CH₂—Ar), 5.42 (d, J=14 Hz, 1 H, —O—CH₂-Ar , 5.85 (dd, J=2.5 Hz, J=1 Hz, 1 H, 5-H), 7.61 (d, J=8.5 Hz, 2 H, Ar-H), 8.17 (d. J=8.5 Hz, 2 H, Ar-H). IR spectrum in methylene chloride: 2955, 1804, 1715, 1610, 1585, 1525, 1350, 1315, 1200, 1165, 1145, 1120, 1080, 1040, 1025, 1015, 885, 855, 840 cm⁻¹. UV spectrum in dioxane: λ$_{max}$=277 nm (C=15340). cl Step E: 3-tert-Butyl-7-oxo-1-azabicyclo[3.2.0]-hept-2-ene-2-carboxylic acid, Na salt

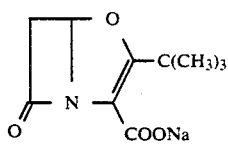

A solution of 17.3 mg (50 μmol) of p-nitrobenzyl 3-tert-butyl-7-oxo-4-oxa-1-azabicyclo-[3.2.0]-hept-2-ene-2-carboxylate in 1 ml of ethyl acetate is introduced via a septum into a mixture of 30 mg of palladium on carbon (10 %), 2 ml of ethyl acetate and a solution of 4.7 mg (56 μmol) of sodium hydrogencarbonate in 1 ml of water cooled to 0° C. in a hydrogen atmosphere and the mixture is hydrogenated. 5.4 ml of hydrogen are consumed in the course of 20 minutes, somewhat more than the theoretically required amount (4.6 ml). The multiphasic mixture is filtered with cooling and the cooled (0° C.) filtrate is washed twice with 3 ml each of ethyl acetate. The aqueous solution is immediately lyophilized in a high vacuum, 8.8 mg of a white solid being obtained: UV (H₂O): H₂O): λ$_{max}$=269 nm (ε=5800) 360 MHz-¹H-NMR spectrum in D₂O: δ=1.23 (s, 9 H, tert-butyl), 3.43 (dd, J=18 Hz, J=1 Hz, 1 H, 6-H trans-position), 3.72 (dd, J=18 Hz, J=2.5 Hz, 1 H, 6-H cis-position), 5.82 (s, 1H, 5-H).

EXAMPLE 2

Preparation of 2-tert-butyl-6-methyl-1-oxapen-2-em-3-carboxylic acid, its p-nitrobenzyl ester and its sodium salt

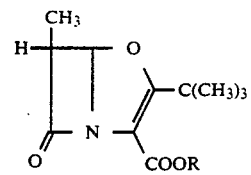

R = H, Na, p-NBz

Starting from 4-acetoxy-3-methylazetidin-2-one, p-nitrobenzyl 2-(4-tert-butylthio-3-methyl-2-oxo-1-azetidinyl)-4,4-dimethyl-3-oxopentanoate

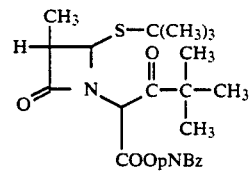

was obtained as a non-crystalline solid via steps A₁, B and C by the process described in Example 1 and using the same reaction conditions. IR spectrum in methylene chloride: 2955, 1765, 1760, 1720, 1610, 1525, 1460, 1380, 1365, 1350, 1315, 1205, 1180, 1120, 1050, 855 840 cm⁻¹. UV spectrum in ethanol: λ$_{max}$=264 nm (ε=10160).

Step D : p-Nitrobenzyl 2-(4-chloro-3-methyl-2-oxo-1-azetidinyl)-4,4-dimethyl-3-oxopentanoate

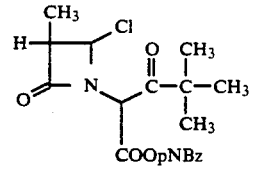

Starting from p-nitrobenzyl 2-(4-tert-butylthio-3-methyl-2-oxo-1-azetidinyl)-4,4-dimethyl-3-oxopentanoate, the title compound (Step D₁) was obtained as a non-crystalline solid (mixture of two diastereomers) by the process described in Example 1 and using the same reaction conditions. NRM spectrum in CD₃CN: δ=1.19, 1.21 and 1.32 (3 signals, 12 H), 3.59-3.98 (m, 1 H), 5.30 (s, 2H), 5.50 (s,~0.25 H), 5.70 (s,~0.75 H), 5.94 d, J=5 Hz,~0.25 H), 6.09 (d, J=5 Hz,~0.75 H), 7.43-7.64 (m, 2H), 8.17 (d, J=9 Hz, 2 H).

Step D₂: p-Nitrobenzyl 2-tert-butyl-6-methyl-1-oxapen-2-em-3-carboxylate (p-nitrobenzyl 3-tert-butyl-7-oxo-4-oxa-1-azabicyclo[3.2.0]hept-2-ene-2-carboxylate)

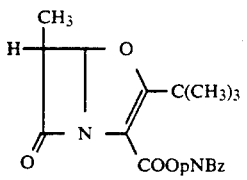

Starting from p-nitrobenzyl 2-(4-chloro-3-methyl-2-oxo-1-azetidinyl)-4,4-dimethyl-3-oxopentanoate, the title compound was obtained as a non-crystalline solid (mixture of cis/trans isomers) by the process described in Example 1 and using the same reaction conditions. IR spectrum in CH₂Cl₂: 2965, 1700, 1715, 1585, 1525, 1345, 1310, 1165, 1140, 1085, 1025, 1015, 935, 850 cm⁻¹. UV spectrum in dioxane: $\lambda_{max}=277$ nm ($\epsilon=15200$).

Step E:
3-tert-Butyl-6-methyl-7-oxo-4-oxa-1-azabicyclo[3.2.0]-hept-2-ene-2-carboxylate. Na salt

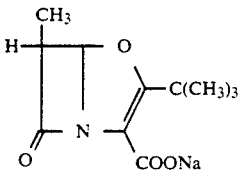

Starting from p-nitrobenzyl 3-t-butyl-6-methyl-7-oxo-4-ox -1-azabicyclo[3.2.0]hept-2-ene-2-carboxylate, the title compound was obtained as a white solid (lyophlizate) ilizate) by the process described in Example 1 and using the same reaction conditions. UV spectrum in H₂O: $\lambda_{max}=260$ nm (c=5800). ¹H-NMR spectrum in D₂O: 1.24 and 1.27 (2s, 9H), 1.38 (d, J=7.5 Hz), 3.67 (q, J=7.5 Hz,~0.5 H, trans), 3.96 (dq, J=7.5 Hz, J=3 Hz,~0.5 H, cis). 5.55 (s,~0.5 H, trans), 5.80 (d, J=3 Hz,~0.5 Hz, cis).

EXAMPLE 3

Preparation of 2-tert-butyl-6.6-dimethyl-1-oxaoen-2-em-3-carboxylic acid, its p-nitrobenzyl ester and its sodium salt

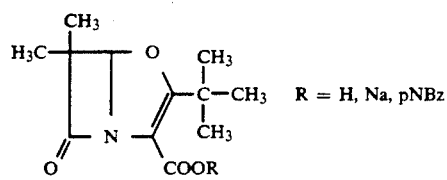

Starting from 4-acetoxy-3,3-dimethylazetidin-2-one via Steps A , B and C. p-nitrobenzyl 2-(4-tert-butylthio-3,3-dimethyl-2-oxo-1-azetidinyl)-4,4-dimethyl-3-oxopentanoate

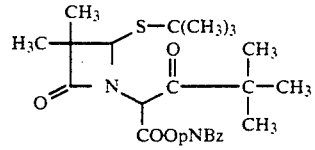

was obtained as a crystalline solid of melting point 87.5°-90.5° C. from methylene chloride/hexane (mixture of two diastereomers) by the process described in Example 1 and using the same reaction conditions. IR spectrum in methylene chloride: 2955, 2865, 1765, 1755, 1715, 1610, 1525, 1460, 1390, 1370, 1350, 1315, 1185, 1135, 1105, 995, 850 cm⁻¹. UV spectrum in ethanol: $\lambda_{max}=264.5$ nm ($\epsilon=10930$).

Step D: p-Nitrobenzyl 3-tert-butyl-6.6-dimethyl-7-oxo-4-oxa-1-azabicyclo[3.2.01]hept-2-ene-2-carboxylate

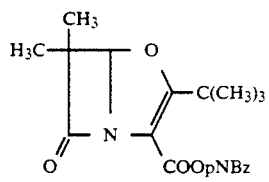

A solution of 930 mg (2.0 mmol) of p-nitrobenzyl 2-(4-tert-butylthio-3,3-dimethyl-2-oxo-1-azetidinyl)-4,4-dimethyl-3-oxopentanoate in 460 ml of dry dimethoxyethane was stirred vigorously together with 1046 mg (5.0 mmol) of yellow mercury(II) chloride and heated to reflux for three hours. After cooling, the yellowish solution was filtered through Celite and concentrated to about a tenth of its volume. After diluting with 500 ml of benzene and allowing to stand for two days at 0° C., the solution was filtered off from the resultant colorless precipitate and the clear solution obtained was washed with 250 ml of saturated sodium chloride solution, 250 ml of 0.5 M phosphate buffer solution pH 7 and 250 ml of saturated sodium chloride solution. Drying the organic phase with magnesium sulphate, concentrating the solution to 50 ml and allowing to stand at 0° C., filtering off a little freshly produced precipitate and stripping off the solvent in vacuo gave a yellow, slightly turbid oil. Chromatography of the crude product on 25 g of Florisil using benzene/ethyl acetate (7:1) yielded 560 mg of pure title compound. After recrystallization from methylene chloride/hexane, the melting point is 119°-120.5° C. IR spectrum in methylene chloride: 2935, 2870, 1797, 1715, 1610, 1585, 1525, 1460, 1350, 1315, 1155, 1140, 1085, 1010, 850 cm⁻¹, UV spectrum in dioxane: $\lambda_{max}=278$ nm ($\epsilon=14980$). Mass spectrum (20eV, 80° C.): 374 M⁺. An X-ray structural analysis, which confirms the structure, was carried out on this substance. Step E: 3-tert-Butyl-6.6-dimethyl-7-oxo-4-oxa-1-aza-bicyclo[3.2.01]hept-2-ene-2-carboxylic acid, Na salt

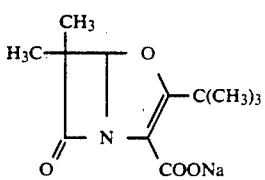

Starting from p-nitrobenzyl 3-tert-butyl-6,6-dimethyl-7-oxo-3-oxa-1-azabicyclo[3.2.0]hept-2-ene-2-carboxylate, the title compound was obtained as a pale yellow solid (lyophilizate) by the process described in Example 1 and using the same reaction conditions. UV spectrum in H$_2$O: $\lambda_{max}$=261 nm. NMR spectrum in D$_2$O: 1.23 (s, 9H), 1.26 (s, 3H), 1.39 (s, 3H), 5.50 (s, 1H).

EXAMPLE 4

Preparation of 2-(2-chloro-1,1-dimethylethyl)-6,6-dimethyl-1-oxapen-2-em-3-carboxylic acid, its p-nitrobenzyl ester and its Na salt

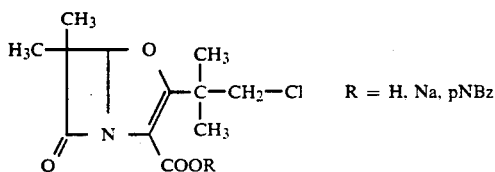

R = H, Na, pNBz

Starting from 4-acetoxy-3,3-dimethylazetidin-2-one via Steps A$_1$, B, C and D and using chloropivaloyl chloride in Step C, the compound

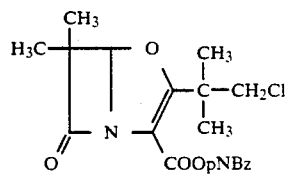

was obtained as a non-crystalline solid by the process described in Example 3 and using the same reaction conditions. IR spectrum in methylene chloride: 2930, 2875, 1803, 1710, 1590, 1525, 1460, 1370, 1350, 1315, 1255, 1160, 1130, 1115, 1090, 1010, 990, 920, 850 cm$^{-1}$.

Step E:

3-(2-Chloro-1,1-dimethylethyl)-6,6-dimethyl7-oxo-4-oxa-1-azabicyclo[3.2.0]hept-2-ene-2-carboxylic acid, Na salt

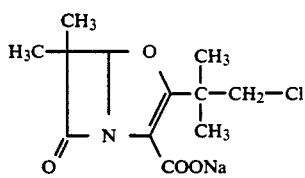

Starting from the corresponding p-nitrobenzyl ester, the title compound was obtained after lyophilization in 60 % yield as a non-crystalline colorless solid by the process given in Example 3. NMR spectrum in D$_2$O: $\delta$=1.27, 1.30, 1.33 and 1.39 (4s, 12H), 3.74 (d, J=10 Hz, 1 H), 4.05 (d, J=10 Hz, 1 H), 5.52 (s, 1 H). UV spectrum in H$_2$O: $\lambda_{max}$ =265 nm ($\epsilon$=5800).

EXAMPLE 5

Preparation of 6,6-dimethyl-3-(1-methyl-1-phenylethyl)-7-oxo-4-oxa-1-azabicyclo[3.2.0]hept-2-ene-2-carboxylic acid, its Na salt and its p-nitrobenzyl ester

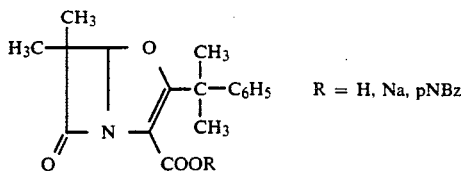

R = H, Na, pNBz

Starting from p-nitrobenzyl 2-(4-tert-butylthio-3,3-dimethyl-2-oxo-azetidinyl)-acetate and 2-methyl-2-phenylpropionyl chloride, the title compound (p-nitrobenzyl ester) was obtained as a non-crystalline slightly yellowish solid by the process described in Example 1 via the Steps C, D$_1$ and D$_2$. IR spectrum in CH$_2$Cl$_2$: 2930, 2875, 1800, 1720, 1600, 1525, 1350, 1320, 1145, 1085, 1075 cm$^{-1}$.

Step E:

6,6-Dimethyl-3-(1-methyl-1-phenylethyl)-7-oxo-4-oxa-1-azabicyclo[3.2.0]hept-2-ene-carboxylic acid, Na salt

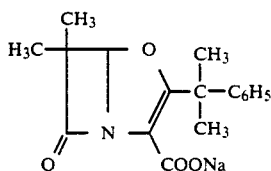

Starting from the corresponding p-nitrobenzyl ester, the title compound was obtained in 50 % yield as a colorless solid after lyophilization by the process described in Example 1. UV spectrum in H$_2$O: $\lambda_{max}$=263 nm ($\epsilon$=5600).

EXAMPLE 6

Preparation of 6,6-dimethyl-3-(1,1-diphenylethyl)-7-oxo-4-oxa-1-azabicyclo [3.2.0]hept-2-ene-2-carboxylic acid, its Na salt and its p-nitrobenzyl ester

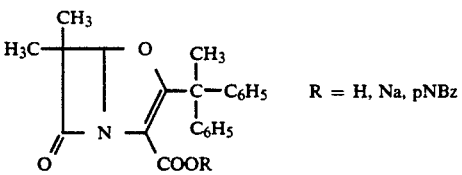

R = H, Na, pNBz

Starting from p-nitrobenzyl 2-(4-tert-butylthio-3,3-dimethyl-2-oxo-azetidinyl)-acetate and 2,2-diphenylpropionyl chloride, the title compound (p-nitrobenzyl ester) was obtained as a colorless solid by the process described in Example 1 via Steps C, D$_1$ and D$_2$. IR spectrum in CH$_2$Cl$_2$: 2930, 2875, 1805, 1725, 1600, 1525, 1350, 1315, 1150, 1085, 1075 cm$^{-1}$.

Step E:
6,6-Dimethyl-3-(1,1-diphenylethyl)-7-oxo-4-oxa-1-azabicyclo3.2.0]-hept-2-ene-carboxylic acid, Na salt

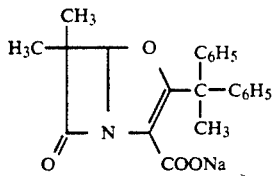

Starting from the corresponding p-nitrobenzyl ester, the title compound was obtained in 63 % yield as a colorless solid after lyophilization by the process described in Example 1. UV spectrum in H₂O: $\lambda_{max}=265$ nm ($\epsilon 6000$).

EXAMPLE 7

Preparation of 6,6-dimethyl-3-[1-methyl-1-(2-thienyl)ethyl-7-oxo-4-oxa-1-azabicyclo[3.2.0]hept-2-ene-2-carboxylic acid, its Na salt and its p-nitrobenzyl ester

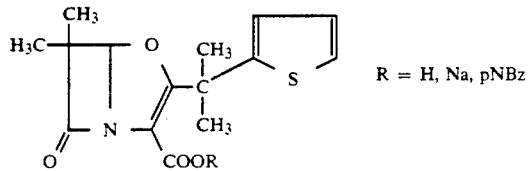

R = H, Na, pNBz

Starting from p-nitrobenzyl 2-(4-tert-butylthio-3,3-dimethyl-2-oxo-azetidinyl)-acetate and 2-methyl-2-thienylpropionyl chloride, the title compound (p-nitrobenzyl ester) was obtained as a slightly yellowish solid by the process described in Example 1 via Steps C, D₁ and D₂. IR spectrum in CH₂Cl₂: 2930, 1795, 1715, 1590, 1520, 1350, 1310, 1140, 1080 cm⁻¹.

Step E:
6,6-Dimethyl-3-[1-methyl-1-(2-thienyl)ethyl-]-7-oxo-4-oxo-1-azabicyclo[3.2.0]hept-2-ene-2-carboxylic acid. Na salt

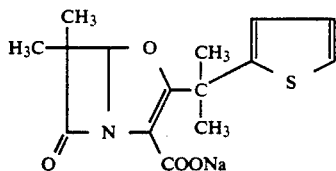

Starting from the corresponding p-nitrobenzyl ester, the title compound was obtained in 70 % yield as a colorless non-crystalline solid (lyophilizate) by the process described in Example 1. UV spectrum in H₂O: $\lambda_{max}=270$ nm ($\epsilon=6,500$).

EXAMPLE 8

Preparation of3-(2-amino-1,1-dimethylethyl)-7-oxo-4-oxa-1-azabicyclo3.2.0[hept-2-ene-2-carboxylic acid

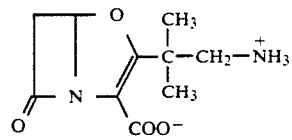

Step C: p-Nitrobenzyl 2-(4-tert-butylthio-2-oxo-1-azetidinyl)-5-chloro-4,4-dimethyl-3-oxopentanoate

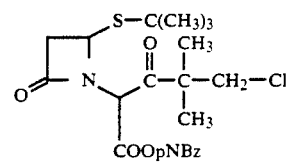

6 ml of a 1 M solution of lithium bis(trimethylsilyla-mide) in THF is slowly added dropwise with stirring at −70° C. to a mixture of 1.06 g (3 mmol) of p-nitrobenzyl 2-(4-tert-butyl-thio-2-oxo-1 -azetidinyl)-acetate and 410 μl (3.17 mmol) of chloropivaloyl chloride in 38 ml of absolute tetrahydrofuran and the mixture is stirred for a further 30 minutes at −70° C. The reaction mixture is diluted with 250 ml of toluene, and 10 ml of 2 N aqueous HCl and 100 ml of saturated NaCl solution are added. After separation, the organic phase is again washed with 100 ml of saturated NaCl solution, then dried over MgSO₄ and filtered, and the solvent is removed on a vacuum rotary evaporator. The non-crystalline residue is chromatographed on 46 g of silica gel using toluluene/ethyl acetate (19:1), 980 mg of non-crystalline title compound being obtained. IR in CH₂Cl₂: 2930, 1770, 1760, 1725, 1615, 1530, 1465, 1370, 1250, 1215, 1190, 1110, 1040, 1000, 847 cm⁻¹.

Conversion of a group R³; p-nitrobenzyl 5-azido-2-(4-tertbutylthio-2-oxo-1-azetidinyl)4,4-dimethyl-3-oxopentanoate

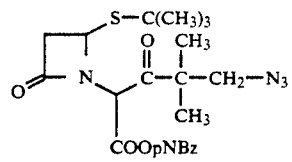

A mixture of 236 mg (0.5 mmol) of p-nitrobenzyl 2-(4-tert-butylthio-2-oxo-1-azetidinyl)-5-chloro-4,4-dimethyl-3-oxopentanoate and 200 mg (1.04 mmol) of Triton B azide in 0.3 ml of DMF is stirred at room temperature during the course of 20 hours, then diluted with toluene and washed twice with water. The aqueous phase is extracted using a little toluene and the combined organic phases are dried over MgSO₄. Filtration and evaporation of the solvent in vacuo yields 290 mg of a colorless residue. IR spectrum in CH₂Cl₂: 2930, 2860, 2110, 1775, 1755, 1720, 1610, 1530, 1350, 1180, 1120, 850 cm⁻¹.

Step D₁: p-Nitrobenzyl 5-azido-2-(4-chloro-2-oxo-1-azetidinyl)-4,4-dimethyl-3-oxopentanoate

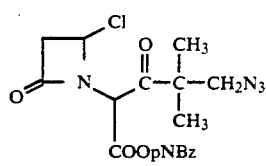

286 μl of a solution of chlorine in carbon tetrachloride containing 1.14 g/10 ml is added at −60° C. to a solution of 110 mg of p-nitrobenzyl 5-azido-2-(4-tert-butylthio-2-oxo-1-azetidinyl)-4,4-dimethyl-3-oxopentanoate in 9 ml of methylene chloride. The reaction solution is evaporated in a rotary evaporator, 119 mg of yellow oil being obtained. IR spectrum in $CH_2Cl_2$: 2930, 2860, 2105, 1780, 1755, 1720, 1610, 1530, 1350, 1190 cm$^{-1}$.

Step D₂: p-Nitrobenzyl 3-(2-azido-1,1-dimethylethyl)-7-oxo-4-oxa-1-azabicyclo[3.2.0]hept-2-ene-2-carboxylate

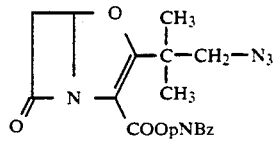

313 μl of a 0.75 M solution of potassium tert-butoxide in tert-butanol are added at −30° C. to a solution of 107 mg (0.23 mmol) of p-nitrobenzyl 5-azido-2-(4-chloro-2-oxo-1-azetidinyl)-4,4-dimethyl-3-oxopentanoate in 4.5 ml of dry tetrahydrofuran and the solution is stirred at −30° C. during the course of 30 minutes. The reaction mixture is then diluted with 20 ml of ethyl acetate, and the mixture is washed with 10 ml of water and 10 ml of NaCl solution. The aqueous phases are extracted using 10 ml of ethyl acetate and the combined organic phases are dried over MgSO₄, filtered and then evaporated in vacuo. In this way, 105 mg of a yellow residue are obtained which is crystallized from methylene chloride/ diisopropyl ether. Yield 61 mg of melting point 81°-82° C. IR spectrum in $CH_2$—$Cl_2$: 2950, 2860, 2110, 1810, 1720, 1590, 1530, 1370, 1320, 1085, 1020 cm$^{-1}$.

Step E: 3-(2-Amino-1,1-dimethylethyl)-7-oxo-4-oxa-2-azabicyclo[3.2.0]hept-2-ene-2-carboxylic acid

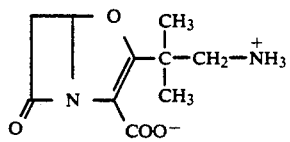

A solution of 21 mg (0.054 mmol) of p-nitrobenzyl 3-(2-azido-1,1-dimethylethyl)-7-oxo-4-oxa-1-azabicyclo-[3.2.0]hept-2-ene-2-carboxylate in 1 ml of ethyl acetate is added at 0° C. through a septum using a syringe to a prehydrogenated mixture of 60 mg of palladium on carbon (10 %) in 1 ml of ethyl acetate and 0.7 ml of water. After a reaction time of 20 minutes, 5.7 ml of hydrogen are absorbed (theoretical amount: 4.9 ml). The reaction mixture is filtered at 0° C. and the aqueous phase is washed twice with 2 ml of precooled ethyl acetate. The aqueous phase contains 8.96 mg of the title compound. UV spectrum in $H_2O$: $\lambda_{max}$=271 nm ($\epsilon$=5000).

EXAMPLE 9

Preparation of 3-[1,1-dimethyl-2-((1-methyl-1,2,3,4-tetrazol-5-yl)-thio)-ethyl]-7-oxo-4-oxa-1-azabicyclo[3.2.0]hept-2-ene-carboxylic acid, its Na salt and its p-nitrobenzyl ester

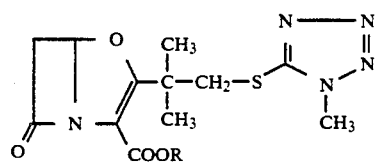

R = H, Na pNBz

Conversion of a group R³; p-nitrobenzyl 2-(4-tert-butylthio-2-oxo-1-azetidinyl)-4,4-dimethyl-5-[(1-methyl-1,2,3,4-tetrazol-5-yl)-thio]-3-oxopentanoate

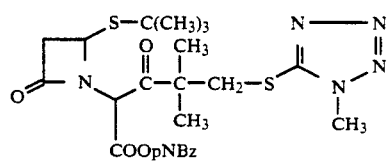

A mixture of 118 mg (0.25 mmol) of p-nitrobenzyl 2-(4-tert-butylthio-2-oxo-1-azetidinyl)-5-chloro-4,4-dimethyl-3-oxopentanoate and 82 mg (0.59 mmol) of 1-methyl-5-mercapto-1,2,3,4-tetrazole Na salt are stirred in 0.2 ml of dimethylformamide during the course of 20 hours at room temperature. The reaction mixture is chromatographed directly on a chromatography column containing 6 g of silica gel using toluene-/ethyl acetate (19:1), 60 mg of pure title compound being obtained as a non-crystalline solid.

Step D₁ and D₂: p-Nitrobenzyl 3-[1.1-dimethyl-2-((1-methyl-1,2,3,4-tetrazol-5-yl)-thio)ethyl]-7-oxo-4-oxa-1-azabicyclo[3.2.0]-hept-2-ene-2-carboxylate

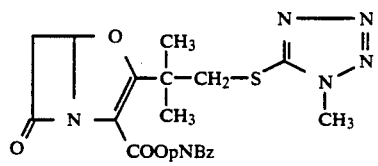

Starting from p-nitrobenzyl 2-(4-tert-butylthio-2-oxo-1-azetidinyl)-4,4-dimethyl-5-[(1-methyl-1,2,3,4-tetrazol-5-yl)thio]-3-oxo-pentanoate, the title compound was obtained via Steps D₁ and D₂ by the process given in Example 1 after chromatography on silica gel using toluene/ethyl acetate (3:1). IR spectrum in $CH_2Cl_2$: 2930, 2860, 1810, 1720, 1590, 1525, 1350, 1320, 1175, 1120, 1030, 1015 cm$^{-1}$.

Step E:

3-[1,1-Dimethyl-2-((1-methyl-1,2,3,4-tetrazol-5-yl)-thio)-ethyl]-7-oxo-4-oxa-1-azabicyclo[3.2.0]-hept-2-ene-2-carboxylic acid, Na salt

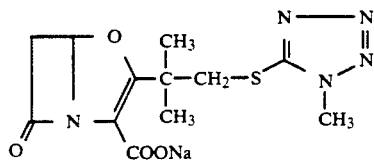

Starting from the corresponding p-nitrobenzyl ester, the title compound was obtained via Step E by the process described in Example 1 as a white solid (after lyophilization). UV spectrum in H₂O: strong end absorption, shoulder at 270 nm , ($\epsilon$=4000).

EXAMPLE 10

Preparation of 3-methyl-1-(2-thienyl)-ethyl]-7-oxo-4-oxa-1-azabicyclo[3.2.0]hept-2-ene-2-carboxylic acid, its Na salt and its p-nitrobenzyl ester

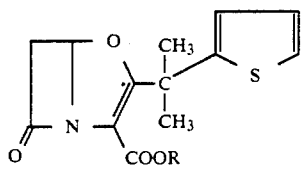

R = H. Na, pNBz

Starting from p-nitrobenzyl 2- 4-tert-butylthio-3,3-dimethyl-2-oxoazetidinyl)-acetate and 2-methyl-2-thienylpropionyl chloride, the title compound (p-nitrobenzyl ester) was obtained via Steps C, D₁ and D₂ by the process described in Example 1 as a colorless non-crystalline solid. IR spectrum in CH₂Cl₂: 2930, 1800, 1720, 1605, 1530, 1350, 1080 cm⁻¹.

Step E:

3-[1-Methyl-1-(2-thienyl)-ethyl]-7-oxo-4-oxa-1-azabicyclo 3.2.0]hept-2-ene-2-carboxylic acid, Na salt

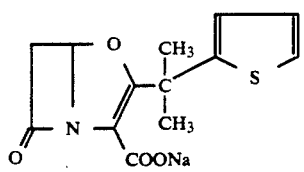

Starting from the corresponding p-nitrobenzyl ester, the pure title compound was obtained as a white solid by the process described in Example 1. UV spectrum in H₂O: $\lambda_{max}$=270 nm ($\epsilon$=6500).

EXAMPLE 11

Preparation of 2-(2-acetoxy-1,1-dimethylethyl)-7-oxo-4-oxa-1-azabicyclo [3.2.0]hept-2-ene-2-carboxylic acid, its Na salt and its p-nitrobenzyl ester

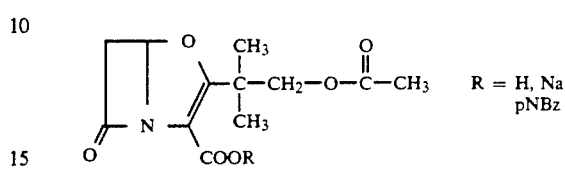

R = H, Na pNBz

Starting from p-nitrobenzyl 2-(4-tert-butylthio-2-oxoazetidinyl)-acetate and β-acetoxypivaloyl chloride, the title compound (p-nitrobenzyl ester) was obtained by the process described in Example 1 via Steps C, D₁ and D₂ as a slightly yellowish non-crystalline solid. IR spectrum in CH₂Cl₂: 2950, 2850, 1810, 1740, 1720, 1590, 1550, 1350, 1080 cm⁻¹.

Step E:

2-(2-Acetoxy-1,1-dimethylethyl)-7-oxo-4-oxa-1-azabicyclo[3.2.0]hept-2-ene-2-carboxylic acid, Na salt

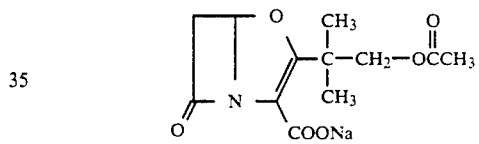

Starting from the corresponding p-nitrobenzyl ester, the title compound was obtained in 70% yield as a non-crystalline white solid (lyophilizate) by the process described in Example 1 via Step E.

UV spectrum in H₂O: $\lambda_{max}$=270 nm ($\delta$=6300. NMR spectrum in D₂O: $\delta$=1.25 (s, 3H), 1.26 (s, 3H) 2.06 (s, 3H), 3.40 (dd, J=1 Hz, J=17 Hz, 2 H) 3.72 (dd, J=3 Hz, J=17 Hz, 2 H) 4.23 (AB, J=17 Hz, 2 H), 5.80 (dd, J=1 Hz, J=3 Hz, 1 H).

EXAMPLE 12

Preparation of 3-tert-butyl-6-(1-hydroxyethyl)-7-oxo-4-oxa-1-azabicyclo [3.2.]hept-2-ene-2-carboxylic acid, its Na salt and its p-nitrobenzyl ester

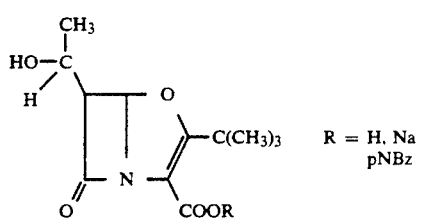

R = H, Na pNBz

Step A₂:
4-Methylthio-3-[1-(p-nitrobenzyloxycarbonyloxy)ethyl]-azetidin-2-one

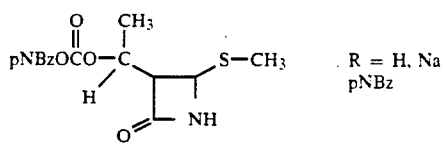

R = H, Na
pNBz 1.17 g (16.7 mmol) of methyl mercaptan Na salt are added at 0° C. to a solution of 4.48 g (11.1 mmol) of 4-(2-hydroxyethylsulphonyl)-3-[1-(p-nitrobenzyloxycarbonyloxy)-ethyl]-azetidin-2-one in 11 ml of acetonitrile and 11 ml of H₂O and the mixture is stirred at 0° C. during the course of 20 minutes. The reaction mixture is diluted with 100 ml of methylene chloride and 25 ml of H₂O and the aqueous phase is extracted three times with 25 ml each of methylene chloride after separating off the organic phase. The purified organic phases are dried over MgSo₄ and filtered, and the solvent is removed in vacuo, 3.80 g of title compound being obtained as a slightly yellowish non-crystalline compound. NMR spectrum in CDCl₃: δ=1.45 (d, J=7 Hz, 3 H). 2.12 (s, 3 H), 3.3 (dd, J=Hz, J=2 Hz), 4.70 (d, J=2 Hz, 1 H), 5.12 (m, 1 H), 5.20 (s, 2 H), 6.45 (wide s, 1 H), 7.50 (d, J=8.5 Hz, 2 H), 820 (d, J=8.5 Hz, 2 H).

Step B: p-Nitrobenzyl 2-[4-methylthio-3-(1-(p-nitrobenzyloxycarbonyloxy)-ethyl)-2-oxoazetidinyl]-acetate

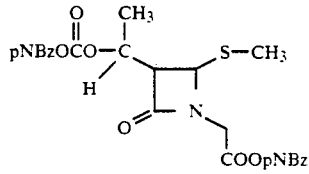

2.2 ml of a 1 M solution of lithium bis-(trimethylsilyl)amide are added with stirring at −70° C. in the course of 5 minutes to a mixture of 680 g (2mmol) of 4-methylthio-3-[1-(p-nitrobenzyloxycarbonyloxy)-ethyl]-azetidin-2-one and 602 mg (2.2 mmol) of p-nitrobenzyl bromoacetate in 2 ml of dry tetrahydrofuran and 2 ml of dry DMF. The reaction mixture is stirred at −70° C. during the course of 30 minutes, diluted with 30 ml of ethyl acetate and 70 ml of toluene and washed twice with dilute NaCl solution. The organic phase is dried over MgSO₄ and filtered, and the solvent is evaporated in vacuo. The residue is chromatographed on 65 g of silica gel using toluene/ethyl acetate 4:1, 520 mg of a yellow oil being obtained. IR spectrum in CH₂Cl₂: 2920, 2850, 1765, 1750, 1605, 1520, 1355, 1345 cm⁻¹.

Step C: p-Nitrobenzyl 4,4-dimethyl-2-[4-methylthio-3-(1-(p-nitrobenzyloxycarbonyloxy)-ethyl)-2-oxo-azetidinyl]-3-oxopentanoate

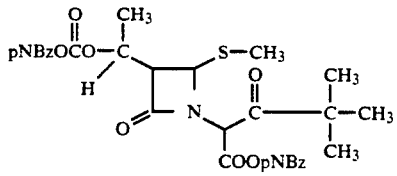

1.1 ml of 1 M lithium bis(trimethylsilyl)-amide are added at −70° C. with stirring in the course of 5 minutes to a mixture of 275 mg (0.515 mmol) of p-nitrobenzyl 2-[4-methylthio-3-(1-(p-nitrobenzyloxycarbonyloxy)-ethyl)-2-oxoazetidinyl]-acetate and 67 μl (0.55 mmol) of pivaloyl chloride in 6.7 ml of dry tetrahydrofuran and the reaction mixture is stirred at −70° C. during the course of a further 30 minutes and then diluted with 40 ml of toluene and with 30 ml of 2 N HCl, then washed twice with 40 ml each of NaCl solution. The organic phase is dried over MgSO₄ and filtered, and the solvent is removed in vacuo. The residue is chromatographed on 10 g of silica gel using toluene/ethyl acetate (9:1), 268 mg of a white non-crystalline solid being obtained. IR spectrum in CH₂Cl₂: 2930, 2850, 1775, 1760, 1720, 1610, 1535, 1350 cm⁻¹.

Step D₁: p-Nitrobenzyl 2-[4-chloro-3-(1-(p-nitrobenzyloxycarbonyloxy)-ethyl)-2-oxoazetidinyl]-4,4-dimethyl-3-oxo-pentanoate

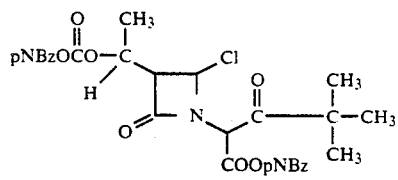

660 μl of a solution of chlorine in carbon tetrachloride containing 850 mg in 10 ml are added at −60° C. to a solution of 244 mg (0.395 mmol) of p-nitrobenzyl 4,4-dimethyl-2-[4-methylthio-3-(1-(p-nitrobenzyloxycarbonyloxy)-ethyl)-2-oxoazetidinyl]-3-oxo-pentanoate-p-nitrobenzoate in 16 ml of methylene chloride. The weakly yellow solution is stirred at −60° C. during the course of 2 hours and the solvent is removed in vacuo, 236 mg of a colorless non-crystalline solid being obtained. IR spectrum in CH₂Cl₂: 2930, 2850, 1795, 1765, 1725, 1620, 1530, 1355 cm⁻¹.

Step D₂ p-Nitrobenzyl 3-tert-butyl-6-[1-(p-nitrobenzyloxycarbonyloxy)-ethyl]-7-oxo-4-oxa-1-azabicyclo[3.2.0]-hept-2-ene-carboxylic acid

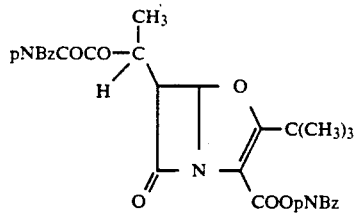

476 μl of 0.75 M potassium tert-butoxide in tert-butanol are added at −30° C. with stirring to a solution of 214 mg of p-nitrobenzyl 2-[4-chloro-3-(1-(p-nitrobenzyloxycarbonyloxy)-ethyl)-2-oxoazetidinyl]-4,4-dimethyl-3-oxo-pentanoate in 7 ml of dry tetrahydrofuran and the reaction mixture is then stirred at −30° C. during the course of 30 minutes. The reaction solution is diluted with 40 ml of ethyl acetate and then washed with 40 ml of dilute NaCl and with 40 ml of saturated NaCl solution. Drying the organic phase over MgSO₄, filtering and evaporating the solvent in vacuo yields 198 mg of residue which is chromatographed on 6 g of silica gel using toluene/ethyl acetate, 183 mg of a colorless non-crystalline solid (title compound) being obtained. IR spectrum in $CH_2Cl_2$: 3030, 2950, 1805, 1755, 1720, 1610, 1580, 1530, 1350, 1320, 1090 cm$^{-1}$.

Step E: Simultaneous removal of two protective groups,
3-tert-butyl-6-(1-hydroxyethyl)-2-oxo-4-oxo-1-azabicyclo[3.2.0]hept-2-ene-2-carboxylic acid, Na salt

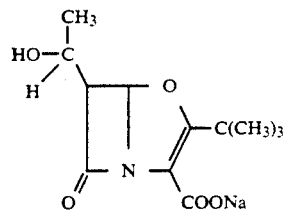

A solution of 28 mg (0.05 mmol) of p-nitrobenzyl 3-tert-butyl-6-[1-(p-nitrobenzylcarbonyloxy)-ethyl]-7-oxo-4-oxa-1-azabicyclo [3.2.0]hept-2-ene-2-carboxylate in 1 ml of ethyl acetate is added at 0° C. through a septum using a syringe to a prehydrogenated mixture of 84 mg Pd/C (10%), 4.6 mg of $NaHCO_3$ in 1 ml of ethyl acetate and 0.7 ml of $H_2O$ and the mixture is hydrogenated at 0° C. during the course of 40 minutes, 8.0 ml of $H_2$ being absorbed (theoretical value about 8.8 ml of $H_2$). The mixture is filtered at 0° C. and the aqueous phase is washed twice more with 2 ml each of precooled ethyl acetate and then lyophilized in a high vacuum, 11 mg of a white non-crystalline solid (title compound) being obtained. UV spectrum in $H_2O$: $\lambda_{max}=278$ nm ($\epsilon=5500$).

EXAMPLE 13

Preparation of 3-tert-butyl-6-hydroxymethyl-7-oxo-4-oxa-1-azabicyclo[3.2.0]hept-2-ene-2-carboxylic acid and its Na salt

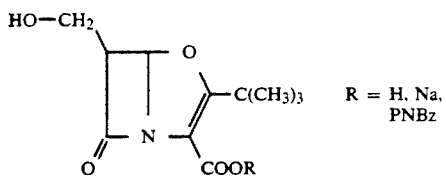

Starting from 4-(2-hydroxyethylsulphonyl)-3-(p-nitrobenzyloxy-carbonyloxymethyl)-azetidin-2-one, the title compound (Na salt) was obtained as a white non-crystalline solid (lyophilized) by the process described in Example 12 via Steps $A_2$, B, C, $D_1$, $D_2$ and E. UV spectrum in $H_2O$: $\lambda_{max}=275$ nm ($\epsilon=5500$).

The potassium salt of 3-tert-butyl-6-hydroxymethyl-7-oxo-4-oxa-1-azabicyclo [3.2.0]-hept-2-ene-2-carboxylic acid was prepared in an analogous manner.

EXAMPLE 14

Preparation of 2-tert-butyl-6-ethylidene-1-oxapen-2-em-3-carboxylic acid, its Na salt and its p-nitrobenzyl ester

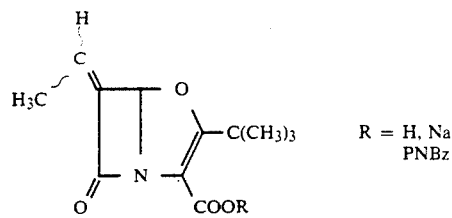

Starting from 4-tert-butylthio-3-ethylideneazetidin-2-one, the title compound (p-nitrobenzyl ester) is obtained via Steps B, C, D and $D_2$ using the reagents and reaction conditions indicated in Example 12 (p-nitrobenzyl 3-tert-butyl-6-ethylidene-3-oxa-7-oxo-1-azabicyclo [3.2.0]hept-2-ene-2-carboxyate.

IR spectrum in $CH_2Cl_2$: 1800, 1720, 1585, 1525 1345, 1310, 1165 cm$^{-1}$.

Step E:
3-tert-Butyl-6-ethylidene-4-oxa-7-oxo-1-azabicyclo [3.2.0]hept-2-ene-2-carboxylic acid, Na salt

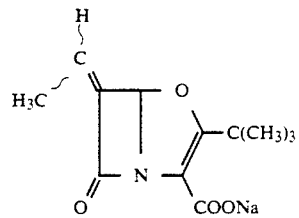

Starting from the corresponding p-nitrobenzyl ester, the title compound is obtained (white lyophilizate) using the reaction conditions indicated in Example 12 and using Pd on $PbCO_3$ instead of Pd on C as a catalyst after a reaction time of 4 hours. UV spectrum in $H_2O$: $\lambda_{max}=272$ ($\epsilon=5100$).

EXAMPLE 15

Production of pharmaceutical preparations

A unit dose form is prepared by mixing 60 mg of 3-tert-butyl-6-hydroxymethyl-7-oxo-4-oxa-1-azabicyclo-3.2.0]hept-2-ene-2-carboxylic acid, K salt with 120 mg of ampicillin, 20 mg of lactose and 5 mg of magnesium stearate and the 205 mg of mixture are added to a No. 3 gelatin capsule. Similarly, if more active constituents and less lactose are used, other dose forms may be prepared and filled into No. 3 gelatin capsules; and should it be necessary to mix more than 205 mg of constituents together, larger capsules, and also compressed tablets and pills, may also be produced. The following examples illustrate the production of pharmaceutical preparations.

TABLE

|  | mg |
|---|---|
| 3-tert-Butyl-6-hydroxymethyl-7-oxo-4-oxa-1-azabicyclo[3.2.0]hept-2-ene-2-carboxylic acid, K salt | 60 |
| Ampicillin | 120 |
| Corn starch V.S.P. | 6 |
| Magnesium stearate | 232 |

| | mg |
|---|---|
| Dicalcium phosphate | 192 |
| Lactose. V.S.P. | 190 |

The active constituents are mixed with the dicalcium phosphate, lactose and about half the corn starch. The mixture is then granulated with 6 mg of corn starch and coarse-sieved. It is dried in a high vacuum and again sieved through sieves having internal mesh widths of 1.00 mm (No. 16 screens). The rest of the corn starch and the magnesium stearate is added and the mixture is pressed to give tablets which each weight 800 mg and have a diameter of about 1.27 cm (0.5 in.).

| Parenteral solution | |
|---|---|
| Ampoule | |
| 3-tert-Butyl-6-hydroxymethyl-7-oxo-4-oxa-1-azabicyclo[3.2.0]heptene-2-carboxylic acid K salt | 100 mg |
| Ampicillin | 500 mg |
| Sterile water (is added from a separate ampoule using a syringe immediately before use) | 2 ml |
| Ophthalmic solution | |
| 3-tert-Butyl-6-hydroxymethyl-7-oxo-4-oxa-1-azabicyclo[3.2.0]heptene-2-carboxylic acid K salt | 20 mg |
| Ampicillin | 100 mg |
| Hydroxypropylmethylcellulose | 5 mg |
| Sterile water to | 1 mg |
| (is added from a separate ampoule using a syringe immediately before use) | |
| Optical solution | |
| 2-tert-Butyl-6-hydroxymethyl-7-oxo-4-oxa-1-azabicyclo[3.2.0]heptene-2-carboxylic acid K salt | 20 mg |
| Ampicillin | 100 mg |
| Benzalkonium chloride | 0.1 mg |
| Sterile water to (is added from a separate ampoule immediately before use with a syringe) | 1 ml |
| Topical cream or ointment | |
| 3-tert-Butyl-6-hydroxymethyl-7-oxo-4-oxa-1-azabicyclo[3.2.0]heptene-2-carboxylic acid K salt | 20 mg |
| Ampicillin | 100 mg |
| Polyethylene glycol 4000 V.S.P. | 400 mg |
| Polyethylene glycol 400 V.S.P. | 0.1 g |

It is understood that the specification and examples are illustrative but not limitative of the present invention and that other embodiments within the spirit and scope of the invention will suggest themselves to those skilled in the art.

We claim:

1. A pharmaceutical preparation comprising an antibacterially effective amount of an antibiotic susceptible to decomposition by a $\beta$-lactamase, a pharmaceutical excipient therefor, and in addition an effective stabilizing amount of an oxapenem-3-carboxylic acid of the formula

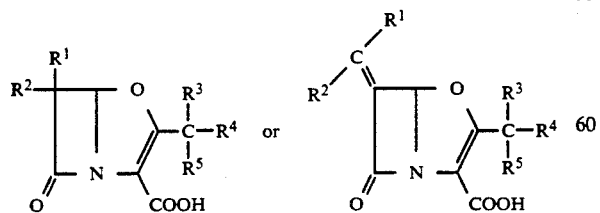

or a pharmaceutically acceptable salt, ester or amide thereof, in which $R^1$ and $R^2$ each independently is hydrogen or pharmaceutically acceptable groups which are bonded to the remaining part of the molecule via carbon-carbon single bonds and are selected from the group consisting of substituted or unsubstituted alkyl, alkenyl, alkinyl, cycloalkyl, alkylcycloalkyl, alkylcycloalkenyl, cycloalkylalkyl, alkenylcycloalkyl, cycloalkenylalkyl, aryl, aralkyl, aralkenyl, aralkinyl, carboxyl or cyano, where the foregoing alkyl, alkenyl or alkinyl molecule parts contain 1 to 6 carbon atoms, and the cycloalkyl or cycloalkenyl molecule parts contain 3 to 6 carbon atoms and the aryl molecule parts contain 6 to 10 carbon atoms, heterocyclyl, heterocyclylalkyl, heterocyclylalkenyl, heterocyclylalkinyl or alkylheterocyclyl, where the foregoing alkyl, alkenyl or alkinyl molecule parts contain 1 to 6 carbon atoms and the heterocyclic molecule part is monocyclic or bicyclic and contains 3 to 10 ring atoms, of which one or more are selected from the group consisting of oxygen, sulphur and nitrogen, and where the substituents of the abovementioned groups may be protected or unprotected hydroxyl, hydroxyalkoxy, aminoalkoxy, amidinoalkoxy, alkoxy, acyloxy, aryloxy, heterocyclyloxy, carbamoyl, carbamoyloxy, thiocarbamoyl, thiocarbamoyloxy, alkylcarbamoyloxy, alkylthiocarbamoyloxy, mercapto, alkylthio, hydroxyalkylthio, aminoalkylthio, amidinoalkylthio, acylthio, arylthio, alkylheterocyclylthio, hydroxyalkylheterocyclylthio, heterocyclylthio, carbamoylthio, alkylcarbamoylthio, thiocarbamoylthio or alkylthiocarbamoylthio, protected or unprotected amino or monoalkylamino, dialkylamino, oxo, protected or unprotected oximino or alkylamino, cycloalkylamino, arylamino, heterocyclylamino, alkanoylamino, amidino, alkylamidino, ganidino, alkylguanidino, carbamoylamino, alkylcarbamoylamino, thiocarbamoylamino, alkylthiocarbamoylamino, nitro, chlorine, bromine, fluorine, iodine, azido, cyano, alkylsulphinyl, alkylsulphonyl, sulphonamido, sulphamoyloxy, alkylsulphonyloxy or protected or unprotected sulpho, sulphoxy or carboxyl, where the substituents, independently of one another, occur once or several times and their aryl molecule part contains 1 to 6 carbon atoms and their aryl molecule part contains 6 to 10 carbon atoms, and where the heterocyclic molecule part is monocyclic or bicyclic and contains 3 to 10 ring atoms, of which one or more are selected from the group consisting of oxygen, sulphur and nitrogen, and $R^3$, $R^4$ and $R^5$, independently of one another, are selected from the abovementioned, pharmaceutically acceptable groups which are bonded to the remaining part of the molecule via carbon-carbon single bonds.

2. A composition according to claim 1, in which $R^1$ and $R^2$, independently of one another, denote hydrogen, alkyl, protected or unprotected hydroxyalkyl or protected or unprotected dihydroxyalkyl, each having 1 to 6 carbon atoms.

3. A composition according to claim 1, in which $R^3$ and $R^4$ denote methyl, and $R^5$ is selected from the group consisting of $CH_3$,

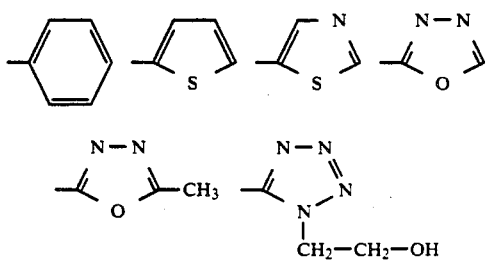

4. A pharmaceutical preparation according to claim 1, in which $R^3$ and $R^4$ denote methyl.

5. A pharmaceutical preparation according to claim 1, wherein the antibiotic is a penem, catapenem or monolactam.

6. A pharmaceutical preparation according to claim 1, wherein the antibiotic is ampicillin, amoxicillin, azlocillin, mazlocillin, tecarcillin, cefopeazon, cephalexin, cefudor, cephaloridine, cefazoline, ceftrazidine, methicillin, mecillinam, penicillin G, aztreonam, formiminothienamycin or moxalactam.

7. A pharmaceutical preparation according to claim 1, wherein the antibiotic comprises penicillin and the oxapenem-3-carboxylic acid component is the potassium salt of 2-tert.-butyl-6-hydroxy-methyloxapenem-3-carboxylic acid.

8. A pharmaceutical preparation according to claim 1, wherein the antibiotic comprises mezlocillin and the oxapenem-3 carboxylic acid component comprises 6-hydroxyethyl-2-tert.-butyl oxapenem-3-carboxylic acid.

9. A method of inhibiting β-lactamase in a patient in need thereof which comprises administering to said patient an amount effective therefor of a pharmaceutical preparation according to claim 1.

* * * * *

UNITED STATES PATENT AND TRADEMARK OFFICE
CERTIFICATE OF CORRECTION

PATENT NO. : 5,108,747

DATED : April 28, 1992

INVENTOR(S) : Pfaendler et al.

It is certified that error appears in the above-identified patent and that said Letters Patent is hereby corrected as shown below:

Title Page &     [54] Title : Delete " OXPENEM " and substitute
Col. 1, line 1       -- OXAPENEM --

Col. 42, line 33    Delete " ganidine " and substitute -- guanidino --

Col. 42, line 40    Delete " aryl " and substitute -- alkyl --

Col. 44, line 44    Delete " mazlocillin, tecarcillin " and substitute -- mezlocillin, ticarcillin --

Signed and Sealed this

Second Day of November, 1993

Attest:

*Attesting Officer*

BRUCE LEHMAN

*Commissioner of Patents and Trademarks*